(12) United States Patent
Xia et al.

(10) Patent No.: US 12,037,576 B2
(45) Date of Patent: Jul. 16, 2024

(54) **RECOMBINANT *BACILLUS SUBTILIS* FOR INCREASING YIELD OF MENAQUINONE 7 AND APPLICATION THEREOF**

(71) Applicant: NANTONG LICHENG BIOLOGICAL ENGINEERING CO. LTD, Jiangsu (CN)

(72) Inventors: Hongzhi Xia, Jiangsu (CN); Long Liu, Jiangsu (CN); Qinqing Gu, Jiangsu (CN); Jiangbo Li, Jiangsu (CN); Shixiu Cui, Jiangsu (CN); Xueqin Lv, Jiangsu (CN); Jianghua Li, Jiangsu (CN); Guocheng Du, Jiangsu (CN); Jian Chen, Jiangsu (CN)

(73) Assignee: NANTONG LICHENG BIOLOGICAL ENGINEERING CO. LTD, Jiangsu (CN)

( * ) Notice: Subject to any disclaimer, the term of this patent is extended or adjusted under 35 U.S.C. 154(b) by 889 days.

(21) Appl. No.: 17/055,607

(22) PCT Filed: Jun. 3, 2020

(86) PCT No.: PCT/CN2020/094048
§ 371 (c)(1),
(2) Date: Nov. 16, 2020

(87) PCT Pub. No.: WO2020/244527
PCT Pub. Date: Dec. 10, 2020

(65) Prior Publication Data
US 2021/0261910 A1 Aug. 26, 2021

(30) Foreign Application Priority Data
Jun. 4, 2019 (CN) .......................... 201910481658.1

(51) Int. Cl.
| | | |
|---|---|---|
| C12N 1/20 | (2006.01) | |
| C12N 9/00 | (2006.01) | |
| C12N 9/12 | (2006.01) | |
| C12N 9/90 | (2006.01) | |

(52) U.S. Cl.
CPC ............. *C12N 1/20* (2013.01); *C12N 9/1294* (2013.01); *C12N 9/90* (2013.01); *C12N 9/93* (2013.01); *C12Y 207/09002* (2013.01); *C12Y 504/04002* (2013.01); *C12Y 602/01005* (2013.01)

(58) Field of Classification Search
None
See application file for complete search history.

(56) References Cited

FOREIGN PATENT DOCUMENTS

| | | |
|---|---|---|
| CN | 108676766 | 10/2018 |
| CN | 108715824 | 10/2018 |
| CN | 108715825 | 10/2018 |

*Primary Examiner* — Brian Gangle
(74) *Attorney, Agent, or Firm* — JCIP GLOBAL INC.

(57) ABSTRACT

The present disclosure provides a recombinant *Bacillus subtilis* for increasing the yield of menaquinone 7 (MK-7) and application thereof, and belongs to the field of genetic engineering. In the present disclosure, 14 recombinant strains BS1-BS14 are constructed through the modification of genes related to the biosynthetic pathway of MK-7 on a chromosome of *Bacillus subtilis*, wherein BS6-BS14 significantly increase the yield of the MK-7, reaching up to 33.5 mg/L, which is 3.53 times the yield of the original strain of wild-type *Bacillus subtilis* 168. The present disclosure further provides a method for modifying the MK-7 biosynthetic pathway in microorganisms to increase the yield of the MK-7, providing a theoretical basis for constructing a high-yielding strain of the MK-7.

10 Claims, 4 Drawing Sheets
Specification includes a Sequence Listing.

US 12,037,576 B2

RECOMBINANT *BACILLUS SUBTILIS* FOR INCREASING YIELD OF MENAQUINONE 7 AND APPLICATION THEREOF

CROSS-REFERENCE TO RELATED APPLICATION

This application is a 371 of international application of PCT application serial no. PCT/CN2020/094048, filed on Jun. 3, 2020, which claims the priority benefit of China application no. 201910481658.1, filed on Jun. 4, 2019. The entirety of each of the above mentioned patent applications is hereby incorporated by reference herein and made a part of this specification.

BACKGROUND

Technical Field

The present disclosure relates to recombinant *Bacillus subtilis* for increasing the yield of menaquinone 7 and application thereof, and belongs to the field of genetic engineering.

Description of Related Art

Vitamin K is an important fat-soluble vitamin. As a cofactor of Y-glutamate carboxylase, vitamin K activates matrix Gla protein to make more calcium deposit in the bones and less calcium deposit in the soft tissues (especially blood vessels), promoting bone development and health, and being able to reverse osteoporosis. For example, vitamin K can help "osteocalcin" combine with essential minerals, protect blood vessels, and prevent atherosclerosis and cardiovascular diseases. In addition to reducing calcium deposition in the blood vessels, vitamin K can also reduce the accumulation of lipoproteins and white blood cells on the blood vessel walls, and can also reduce the death rate of vascular smooth muscle cells, becoming a "vascular guardian".

Vitamin K is a general term for a series of compounds. The core structure of vitamin K is 2-methyl-1,4-menadione ring, but the length and saturation of the side chain structure are different. Vitamin K comprises two forms in nature: vitamin K1 and vitamin K2, wherein vitamin K2 has many subtypes, which are characterized by a variable side chain structure composed of different numbers of isoprenyl groups. This type of vitamin can be referred to as MK-n for short, wherein M stands for menadione, K stands for vitamin K, n stands for the number of isoprenyl groups, and the most common MK-n are MK-4 and MK-7. In blood, MK-7 has a longer half-life than MK-4, and can be better bioavailable. Therefore, due to its long half-life and good bioavailability, MK-7 is more popular in the food, pharmaceutical and healthcare industries, and is widely used as a dietary supplement or medicine to treat osteoporosis, arterial calcification, cardiovascular diseases, cancer, Parkinson's disease, etc.

The isoprene side chains in the chemically synthesized menaquinone 7 (MK-7) molecules are mostly of cis structures, the amount of by-products is big, the source of raw materials is limited, and thus the method has been gradually replaced with biological fermentation. However, the current biological fermentation method for producing MK-7 is mostly limited to solid-state fermentation of natto with *Bacillus natto*. The process requires pre-treatment of natto, and has the defects of many process steps, long fermentation period, complex extraction at a later stage, and low product purity.

*Bacillus subtilis* is widely used in the production of food enzyme preparations and important nutrient chemicals. The products of *Bacillus subtilis* are certified by the FDA as "generally regarded as safe" (GRAS). Therefore, the construction of recombinant *Bacillus subtilis* by metabolic engineering is an effective path for efficiently synthesizing MK-7. However, the synthesis pathway of MK-7 is very complicated, and the metabolic flux of *Bacillus subtilis* in synthesis of MK-7 is insufficient, which will seriously affect the synthesis of MK-7. How to adjust the supply of the metabolic flux of *Bacillus subtilis* to increase the synthesis of MK-7 is a question worthy of further discussion.

SUMMARY

The first objective of the present disclosure is to provide recombinant *Bacillus subtilis* for increasing the yield of menaquinone 7. *Bacillus subtilis* 168 is taken as an original strain; the natural promoters of a menaquinone-specific isochorismate synthase gene menF and a dihydroxynaphthoic acid synthetase gene menB on a chromosome are replaced with $P_{43}$ promoters; the natural promoters of an O-succinylbenzoic acid-CoA ligase gene menE and a transketolase gene tkt on the chromosome are replaced with Phbs promoters; an exogenous isochorismate synthase gene entC and an exogenous phosphoenolpyruvate synthetase gene ppsA are expressed on the chromosome with $P_{43}$ promoters, and a phosphotransferase system (PTS) glucose-specific enzyme IICBA component gene ptsG on the chromosome is knocked out; the sequence of the $P_{43}$ promoter is shown in SEQ ID NO. 3; and the sequence of the Phbs promoter is shown in SEQ ID NO. 5.

In one embodiment, the sequence of the menF gene is shown in SEQ ID NO: 4 (genebank ID: 937190); the sequence of the menB gene is shown in SEQ ID NO: 15 (genebank ID: 937195); the sequence of the menE gene is shown in SEQ ID NO: 16 (genebank ID: 937132); the sequence of the tkt gene is shown in SEQ ID NO: 17 (genebank ID: 937377); the sequence of the entC gene is shown in SEQ ID NO: 18 (genebank ID: 945511); the sequence of the ppsA gene is shown in SEQ ID NO: 19 (genebank ID: 946209); and the sequence of the ptsG gene is shown in SEQ ID NO: 20 (genebank ID: 939255); the sequence of the hepS T gene is shown in SEQ ID NO: 21 (genebank ID: 938998); and the sequence of the fni gene is shown in SEQ ID NO: 22 (genebank ID: 938985).

In one embodiment, the recombinant strain *Bacillus subtilis* 168, $P_{43}$-menF is obtained by replacing the natural promoter of menF on the chromosome of *Bacillus subtilis* with a promoter $P_{43}$ to enhance expression of a menaquinone-specific isochorismate synthase (menF, genebank ID: 937190) gene, and is named BS1.

In one embodiment, the recombinant strain is modified on the basis of BS1 as follows: the natural promoter of a dihydroxynaphthoic acid synthetase (menB, genebank ID: 937195) gene on the chromosome of *Bacillus subtilis* 168 is replaced with a $P_{43}$ promoter to obtain a strain *Bacillus subtilis* 168, $P_{43}$-menF $P_{43}$-menB, named BS2.

In one embodiment, the recombinant strain is modified on the basis of BS2 as follows: the natural promoter of an O-succinylbenzoic acid-CoA ligase (menE, genebank ID: 937132) gene in *Bacillus subtilis* is replaced with a Phbs promoter (with the sequence shown in SEQ ID NO. 5) to obtain *Bacillus subtilis* 168, $P_{43}$-menF $P_{43}$-menB Phbs-menE, named BS3.

In one embodiment, the recombinant strain is modified on the basis of BS3 as follows: an isochorismatase (siderophore specific) (dhbB, genebank ID: 936582) gene on the chromosome of *Bacillus subtilis* is replaced with an isochorismate synthase (entC, genebank ID: 945511) gene derived from *E. coli* K12 and containing a $P_{43}$ promotor to obtain a strain *Bacillus subtilis* 168, $P_{43}$-menF $P_{43}$-menB $P_{hbs}$-menE $P_{43}$-entC ΔdhbB, named BS4.

In one embodiment, the recombinant strain is modified on the basis of BS4 as follows: the natural promoter of a transketolase (tkt, genebank ID: 937377) gene on the chromosome of *Bacillus subtilis* is replaced with a $P_{hbs}$ promoter to finally obtain *Bacillus subtilis* 168, $P_{43}$-menF $P_{43}$-menB $P_{hbs}$-menE $P_{43}$-entC ΔdhbB $P_{hbs}$-tkt, named BS5.

In one embodiment, the recombinant strain is modified on the basis of BS5 as follows: a phosphoenolpyruvate synthetase (ppsA, genebank ID: 946209) gene derived from *E. coli* K12 and containing a $P_{43}$ promotor is integrated between an N-acetylmuramic acid deacetylase (yjeA, genebank ID: 936440) gene and a yjfA (genebank ID: 939830) gene on the chromosome of 10 *Bacillus subtilis*, and a phosphotransferase system (PTS) glucose-specific enzyme IICBA component (ptsG, genebank ID: 939255) gene on the chromosome is knocked out to finally obtain *Bacillus subtilis* 168 $P_{43}$-menF $P_{43}$-menB $P_{hbs}$-menE $P_{43}$-entC ΔdhbB $P_{hbs}$-tkt $P_{43}$-ppsA ΔptsG, named BS6.

In one embodiment, the recombinant strain is modified on the basis of BS6 as follows: a phosphoenolpyruvate synthetase (ppsA, genebank ID: 946209) gene derived from *E. coli* K12 and containing a $P_{43}$ promotor is integrated between an N-acetylmuramic acid deacetylase (yjeA, genebank ID: 936440) gene and a yjfA (genebank ID: 939830) gene on the chromosome of *Bacillus subtilis*, and a phosphotransferase system (PTS) glucose-specific enzyme IICBA component (ptsG, genebank ID: 939255) gene on the chromosome is knocked out to finally construct *Bacillus subtilis* 168 $P_{43}$-menF $P_{43}$-menB $P_{hbs}$-menE $P_{43}$-entC ΔdhbB $P_{hbs}$-tkt $P_{43}$-ppsA ΔptsG $P_{hbs}$-aroG$^{fbr}$, named BS7.

In one embodiment, the recombinant strain is modified on the basis of BS7 as follows: the natural promoter of a shikimate kinase (aroK, genebank ID: 938343) gene on the chromosome of *Bacillus subtilis* is replaced with a $P_{43}$ promoter to finally construct a strain *Bacillus subtilis* 168 $P_{43}$-menF $P_{43}$-menB $P_{hbs}$-menE $P_{43}$-entC ΔdhbB $P_{hbs}$-tkt $P_{43}$-ppsA ΔptsG $P_{hbs}$-aroG$^{fbr}$$P_{43}$-aroK, named BS8.

In one embodiment, the recombinant strain is modified on the basis of BS8 as follows: the natural promoter of a farnesyl diphosphate synthase (ispA, genebank ID: 938652) gene on the chromosome of *Bacillus subtilis* is replaced with a $P_{hbs}$ promoter to finally construct a strain *Bacillus subtilis* 168 $P_{43}$-menF $P_{43}$-menB $P_{hbs}$-menE $P_{43}$-entC ΔdhbB $P_{hbs}$-tkt $P_{43}$-ppsA ΔptsG $P_{hbs}$-aroG$^{fbr}$$P_{43}$-aroK $P_{hbs}$-ispA, named BS9.

In one embodiment, the recombinant strain is modified on the basis of BS9 as follows: the natural promoter of a heptaprenyl diphosphate synthase component I (hepS/T, genebank ID: 938998) gene on the chromosome of *Bacillus subtilis* is replaced with a $P_{43}$ promoter to finally construct a strain *Bacillus subtilis* 168 $P_{43}$-menF $P_{43}$-menB $P_{hbs}$-menE $P_{43}$-entC ΔdhbB $P_{hbs}$-tkt $P_{43}$-ppsA ΔptsG $P_{hbs}$-aroG$^{fbr}$ $P_{43}$-aroK $P_{hbs}$-ispA $P_{43}$-hepS/T, named BS10.

In one embodiment, the recombinant strain is modified on the basis of BS10 as follows: a 2-dehydro-3-deoxy-phosphogluconate aldolase (kdpG, genebank ID: 33073472) gene derived from *Zymomonas mobilis* is fused with a promoter $P_{hbs}$ and then integrated between a putative uronase (yclG, genebank ID: 938292) gene and a spore germination receptor subunit (gerkA, genebank ID: 938285) gene on the chromosome of *Bacillus subtilis* to construct a strain *Bacillus subtilis* 168 $P_{43}$-menF $P_{43}$-menB $P_{hbs}$-menE $P_{43}$-entC ΔdhbB $P_{hbs}$-tkt $P_{43}$-ppsA ΔptsG $P_{hbs}$-aroG$^{fbr}$::lox72 $P_{43}$-aroK $P_{hbs}$-ispA $P_{43}$-hepS/T $P_{hbs}$-kdpG, named BS11.

In one embodiment, the recombinant strain is modified on the basis of BS11 as follows: the natural promoter of a 1-deoxy-D-xylulose-5-phosphate reductoisomerase (dxr, genebank ID: 939636) gene on the chromosome of *Bacillus subtilis* is replaced with a $P_{43}$ promoter to obtain a strain *Bacillus subtilis* 168 $P_{43}$-menF $P_{43}$-menB $P_{hbs}$-menE $P_{43}$-entC ΔdhbB $P_{hbs}$-tkt $P_{43}$-ppsA ΔptsG $P_{hbs}$-aroG$^{fbr}$ $P_{43}$-aroK $P_{hbs}$-ispA $P_{43}$-hepS/T $P_{hbs}$-kdpG $P_{43}$-dxr, named BS12.

In one embodiment, the recombinant strain is modified on the basis of BS12 as follows: the natural promoter of a 1-deoxyxylulose-5-phosphate synthase (dxs, genebank ID: 938609) gene in *Bacillus subtilis* 168 is replaced with a $P_{43}$ promoter to obtain a strain *Bacillus subtilis* 168 $P_{43}$-menF $P_{43}$-menB $P_{hbs}$-menE $P_{43}$-entC ΔdhbB $P_{hbs}$-tkt $P_{43}$-ppsA ΔptsG $P_{hbs}$-aroG$^{fbr}$ $P_{43}$-aroK $P_{hbs}$-ispA $P_{43}$-hepS/T $P_{hbs}$-kdpG $P_{43}$-dxr $P_{43}$-dxs, named BS13.

In one embodiment, the recombinant strain is modified on the basis of BS13 as follows: the natural promoter of an isopentenyl diphosphate isomerase (typeII) (fni, genebank ID: 938985) gene on the chromosome of *Bacillus subtilis* is replaced with a $P_{43}$ promoter to construct a strain *Bacillus subtilis* 168 $P_{43}$-menF $P_{43}$-menB $P_{hbs}$-menE $P_{43}$-entC ΔdhbB $P_{hbs}$-tkt $P_{43}$-ppsA ΔptsG $P_{hbs}$-aroG$^{fbr}$ $P_{43}$-aroK $P_{hbs}$-ispA $P_{43}$-hepS/T $P_{hbs}$-kdpG $P_{43}$-dxr $P_{43}$-dxs $P_{43}$-fni, named BS14.

The second objective of the present disclosure is to provide a method for producing the menaquinone 7, including performing fermentation production using the recombinant strain.

In one embodiment, the fermentation is to inoculate a fermentation medium with a seed solution of the recombinant strain at an inoculum concentration of 10%-20%.

In one embodiment, the formula of the fermentation medium is as follows (mass percentage): soy peptone 5%, glucose 5%, sucrose 5%, and $KH_2PO_3$ 0.06%.

The present disclosure further provides application of the recombinant strain in preparation of drugs for protecting blood vessels and preventing atherosclerosis and cardiovascular diseases.

Beneficial Effects of the Present Disclosure (1) In the present disclosure, 14 recombinant strains BS1-BS14 are constructed through the modification of genes related to the biosynthetic pathway of the MK-7, wherein BS6-BS14 significantly increase the yield of the MK-7, respectively reaching 15.1 mg/L, 16.2 mg/L, 17.4 mg/L, 19.6 mg/L, 21.2 mg/L, 24.2 mg/L, 26.4 mg/L, 28.2 mg/L, and 33.5 mg/L, which are respectively 1.59, 1.71, 1.83, 2.06, 2.23, 2.55, 2.78, 2.97, and 3.53 times the yield of the original strain of wild-type *Bacillus subtilis* 168.

(2) The present disclosure provides a method for modifying the biosynthetic pathway of the MK-7 in microorganisms to increase the yield of the MK-7, providing a theoretical basis for constructing a high-yielding strain of the MK-7.

Biological Materials

The *Bacillus subtilis* 168 of the present disclosure is purchased from the American Type Culture Collection, and the deposit number is ATCC No. 27370.

TABLE 1

Strain genotype

| Strain | Characteristics |
|---|---|
| BS168 | Wild type |
| BS1 | *Bacillus subtilis* 168, $P_{43}$-menF |
| BS2 | *Bacillus subtilis* 168, $P_{43}$-menF $P_{43}$-menB |
| BS3 | *Bacillus subtilis* 168, $P_{43}$-menF $P_{43}$-menB $P_{hbs}$-menE |
| BS4 | *Bacillus subtilis* 168, $P_{43}$-menF $P_{43}$-menB $P_{hbs}$-menE $P_{43}$-entC ΔdhbB |
| BS5 | *Bacillus subtilis* 168, $P_{43}$-menF $P_{43}$-menB $P_{hbs}$-menE $P_{43}$-entC ΔdhbB $P_{hbs}$-tkt |
| BS6 | *Bacillus subtilis* 168, $P_{43}$-menF $P_{43}$-menB $P_{hbs}$-menE $P_{43}$-entC ΔdhbB $P_{hbs}$-tkt $P_{43}$-ppsA ΔptsG |
| BS7 | *Bacillus subtilis* 168 $P_{43}$-menF $P_{43}$-menB $P_{hbs}$-menE $P_{43}$-entC ΔdhbB $P_{hbs}$-tkt $P_{43}$-ppsA ΔptsG $P_{hbs}$-aroG$^{fbr}$ |
| BS8 | *Bacillus subtilis* 168 $P_{43}$-menF $P_{43}$-menB $P_{hbs}$-menE $P_{43}$-entC ΔdhbB $P_{hbs}$-tkt $P_{43}$-ppsA ΔptsG $P_{hbs}$-aroG$^{fbr}$ $P_{43}$-aroK |
| BS9 | *Bacillus subtilis* 168 $P_{43}$-menF $P_{43}$-menB $P_{hbs}$-menE $P_{43}$-entC ΔdhbB $P_{hbs}$-tkt $P_{43}$-ppsA ΔptsG $P_{hbs}$-aroG$^{fbr}$ $P_{43}$-aroK $P_{hbs}$-ispA |
| BS10 | *Bacillus subtilis* 168 $P_{43}$-menF $P_{43}$-menB $P_{hbs}$-menE $P_{43}$-entC ΔdhbB $P_{hbs}$-tkt $P_{43}$-ppsA ΔptsG $P_{hbs}$-aroG$^{fbr}$ $P_{43}$-aroK $P_{hbs}$-ispA $P_{43}$-hepS/T |
| BS11 | *Bacillus subtilis* 168 $P_{43}$-menF $P_{43}$-menB $P_{hbs}$-menE $P_{43}$-entC ΔdhbB $P_{hbs}$-tkt $P_{43}$-ppsA ΔptsG $P_{hbs}$-aroG$^{fbr}$ $P_{43}$-aroK $P_{hbs}$-ispA $P_{43}$-hepS/T $P_{hbs}$-kdpG |
| BS12 | *Bacillus subtilis* 168 $P_{43}$-menF $P_{43}$-menB $P_{hbs}$-menE $P_{43}$-entC ΔdhbB $P_{hbs}$-tkt $P_{43}$-ppsA ΔptsG $P_{hbs}$-aroG$^{fbr}$ $P_{43}$-aroK $P_{hbs}$-ispA $P_{43}$-hepS/T $P_{hbs}$-kdpG $P_{43}$-dxr |
| BS13 | *Bacillus subtilis* 168 $P_{43}$-menF $P_{43}$-menB $P_{hbs}$-menE $P_{43}$-entC ΔdhbB $P_{hbs}$-tkt $P_{43}$-ppsA ΔptsG $P_{hbs}$-aroG$^{fbr}$ $P_{43}$-aroK $P_{hbs}$-ispA $P_{43}$-hepS/T $P_{hbs}$-kdpG $P_{43}$-dxr $P_{43}$-dxs |
| BS14 | *Bacillus subtilis* 168 $P_{43}$-menF $P_{43}$-menB $P_{hbs}$-menE $P_{43}$-entC ΔdhbB $P_{hbs}$-tkt $P_{43}$-ppsA ΔptsG $P_{hbs}$-aroG$^{fbr}$ $P_{43}$-aroK $P_{hbs}$-ispA $P_{43}$-hepS/T $P_{hbs}$-kdpG $P_{43}$-dxr $P_{43}$-dxs $P_{43}$-fni |

Table 2 Sequence List

| Sequence | No. | genebank ID |
|---|---|---|
| Upstream homologous arm sequence menF-up of menF gene | SEQ ID NO: 1 | |
| lox71-zeo-lox66 cassette | SEQ ID NO: 2 | |
| $P_{43}$ promoter sequence | SEQ ID NO: 3 | |
| menF gene segment | SEQ ID NO: 4 | 937190 |
| $P_{hbs}$ promoter | SEQ ID NO: 5 | |
| aroG$^{fbr}$ or gene | SEQ ID NO: 6 | |
| menB gene | SEQ ID NO: 15 | 937195 |
| menE gene | SEQ ID NO: 16 | 937132 |
| tkt gene | SEQ ID NO: 17 | 937377 |
| entC gene | SEQ ID NO: 18 | 945511 |
| ppsA gene | SEQ ID NO: 19 | 946209 |
| ptsG gene | SEQ ID NO: 20 | 939255 |
| HepS/T gene | SEQ ID NO: 21 | 938998 |
| fni gene | SEQ ID NO: 22 | 938985 |

DESCRIPTION OF THE EMBODIMENTS

Figure 1:
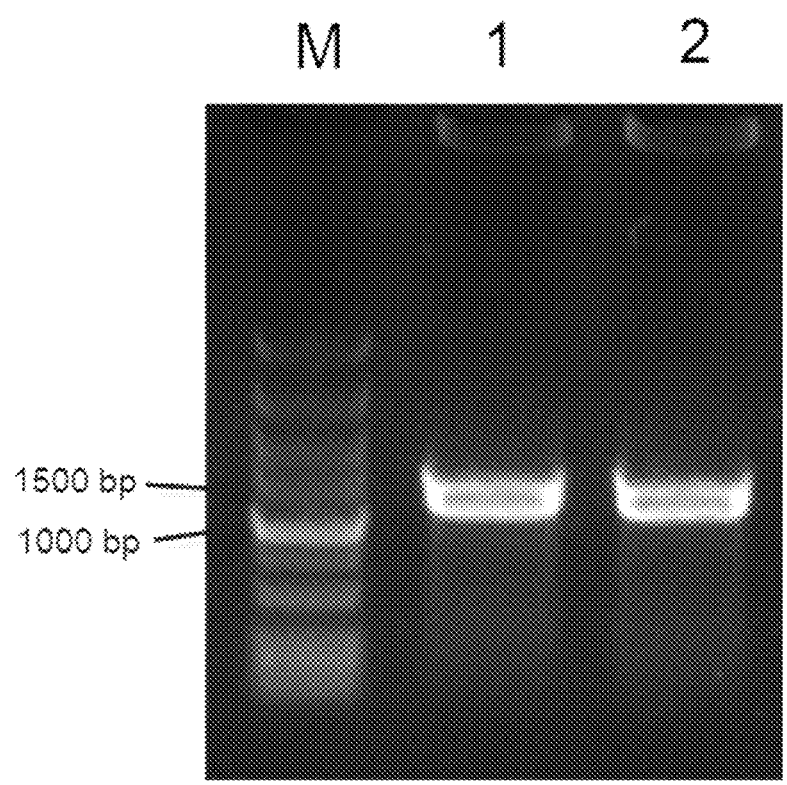
FIG. 1: BS1 colony PCR verification result; M: marker; 1: colony PCR result; and 2: colony PCR result.
Figure 2:
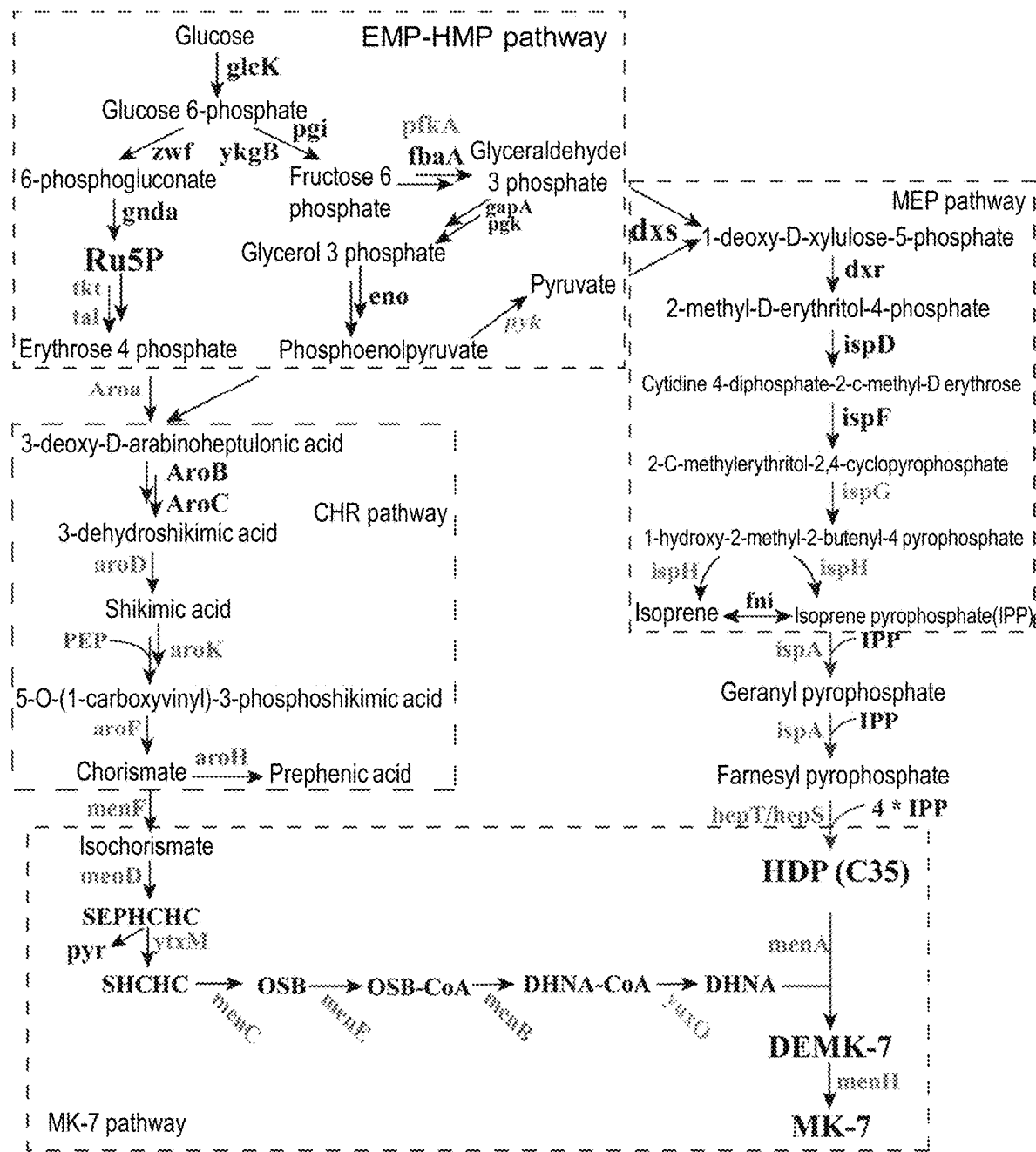
FIG. 2: Synthesis pathway of MK-7 in *Bacillus subtilis*.
Figure 3:
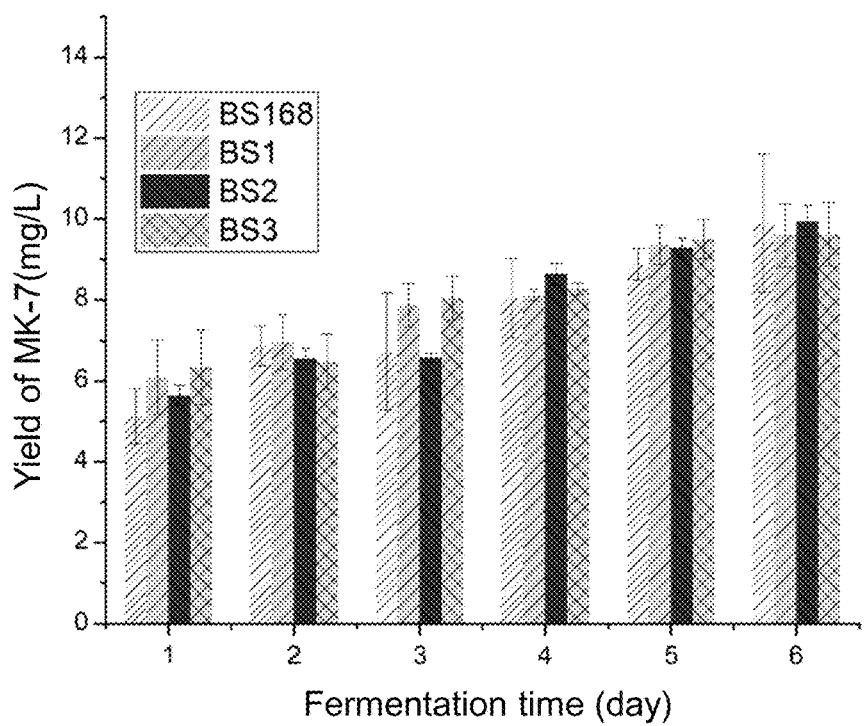
FIG. 3: The effect of enhanced enzyme expression level in the MK-7 synthesis pathway on the yield.
Figure 4:
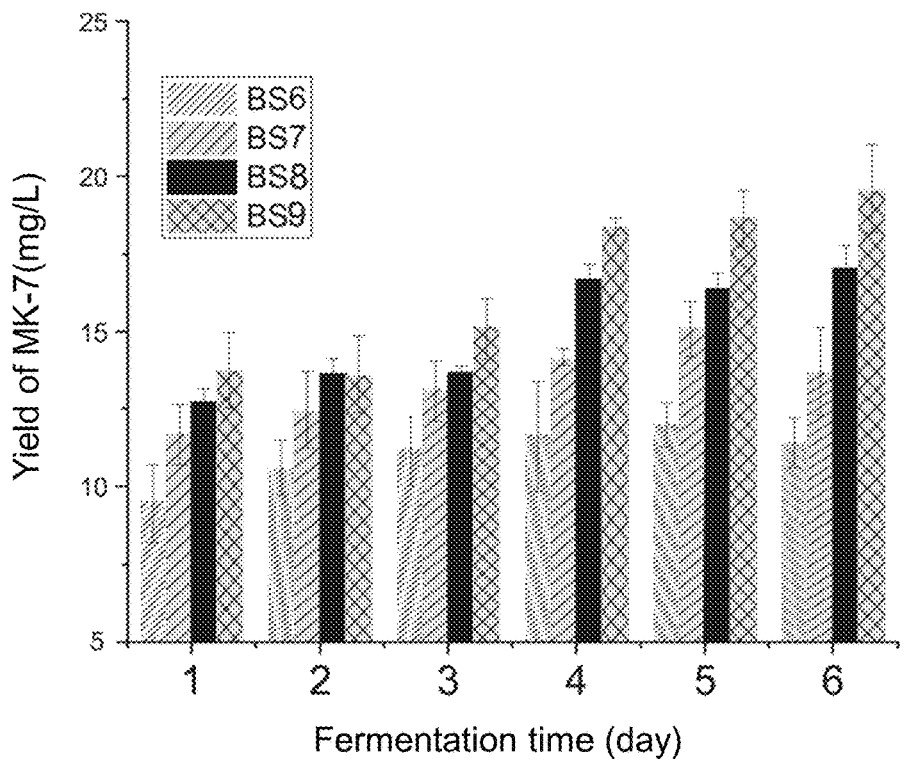
FIG. 4: The effect of enhanced chorismate pathway on the yield of MK-7.
Figure 5:
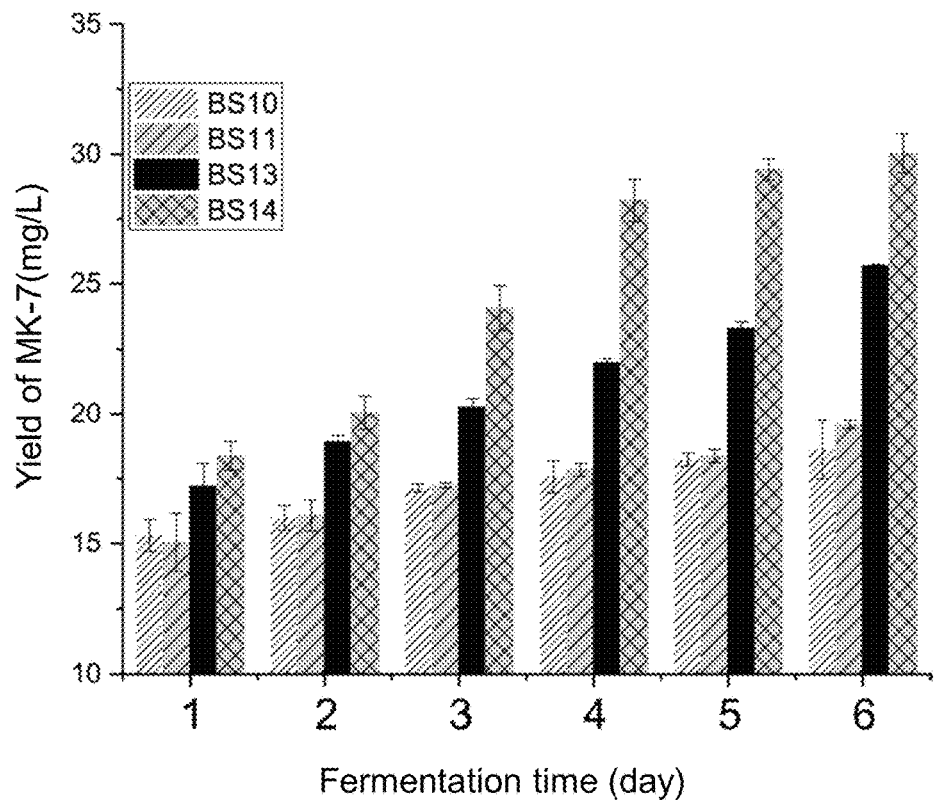
FIG. 5: The effect of enhanced isoprene synthesis on the yield of MK-7.
Figure 6:
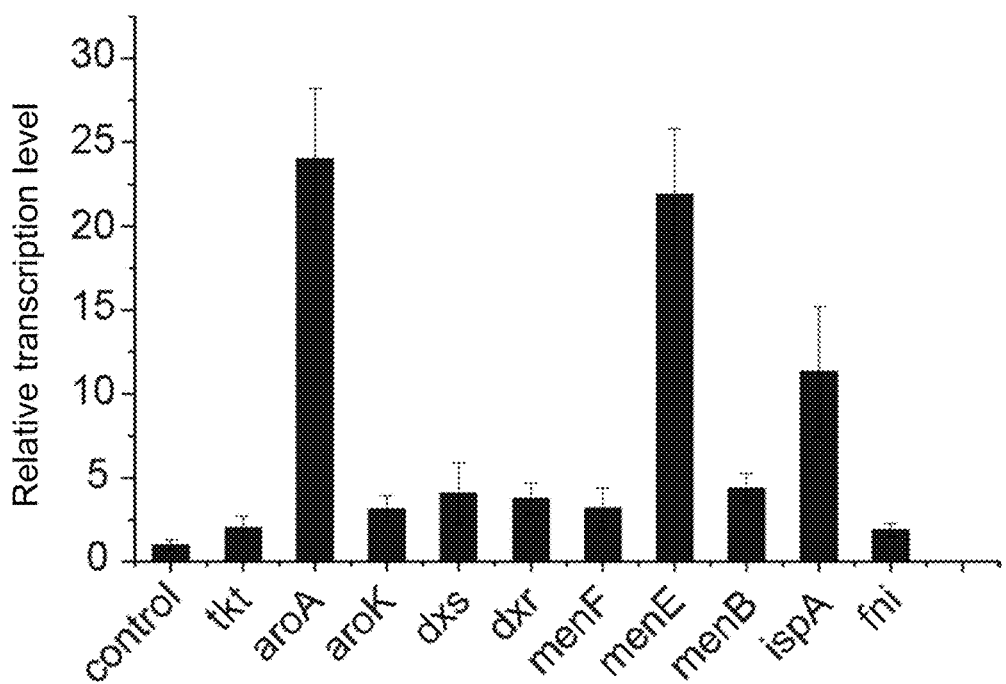
FIG. 6: Analysis on the relative expression of overexpressed genes.

MK-7 detection method: A mixture of isopropanol and n-hexane (1:2 v/v) 4 times fermentation broth is added to the fermentation broth, vortex shaking is performed for 30 min for extraction, and the extract is filtered out and centrifuged at 8,000 r/min for 15 min. The supernatant is collected. At this time, MK-7 is dissolved in the phase, and the supernatant is placed in a refrigerator at −80° C. for freezing to remove lipid crystals. The filtrate is collected and the content of the MK-7 is detected by HPLC.

Detection of MK-7 yield by HPLC: An Agilent ZORBAX EclipseXDB-C18 separation column (5 μm, 250×4.6 mm) is used, the detection temperature is 40° C., the mobile phase uses methanol and dichloromethane (9:1, v/v), the flow rate is 1 mL/min, the detection wavelength is 254 nm, and the injection volume is 10 μL.

Example 1: Construction of Recombinant Strain BS1

The natural promoter of menF on the chromosome of *Bacillus subtilis* was replaced with a constitutive promoter $P_{43}$ to enhance expression of a menaquinone-specific isochorismate synthase (menF, genebank ID: 937190) gene. An unmarked genetic modification strategy was used, referring to the article (Yan, X., Yu, H.-J., Hong, Q., Li, S. P., 2008. Cre/lox system and PCR-based genome engineering in *Bacillus subtilis*. Appl Environ Microb. 74, 5556-5562). The specific construction process was as follows:

(1) Gene Cloning

I. The genome of *Bacillus subtilis* 168 was used as a template, and primers menF-up.FOR and menF-up.REV were used for amplification to obtain the upstream homologous arm sequence menF-up (with the sequence shown in SEQ ID NO. 1) of the menF gene.

II. A lox71-zeo-lox66 cassette containing a bleomycin gene (with the sequence shown in SEQ ID NO. 2) was artificially synthesized.

III. The genome of *Bacillus subtilis* 168 was used as a template, and primers $P_{43}$.For and $P_{43}$.Rev were used for amplification to obtain the $P_{43}$ promoter sequence (with the sequence shown in SEQ ID NO. 3).

IV. The genome of *Bacillus subtilis* 168 was used as a template, and primers menF.FOR and menF.REV were used for amplification to obtain the menF gene segment (with the sequence shown in SEQ ID NO. 4).

(2) Obtaining of Fused Segment

Overlap extension PCR was performed on the four segments: the menF-up, the lox71-zeo-lox66 cassette, the $P_{43}$ promoter sequence, and the menF gene segment obtained in step (1). The PCR conditions were as follows: pre-denaturation was performed at 98° C. for 5 min; then denaturation was performed at 98° C. for 10 s; annealing was performed at 55° C. for 5 s; extension was performed at 72° C. for 2 min; and a total of 30 cycles were performed. The segments of the correct size were recovered by gel extraction to obtain the fused gene segment menF$_{up}$-lox71-zeo-lox66-$P_{43}$-menF.

(3) Homologous Recombination

The fused segment obtained in step (2) was transformed into the competent cell of the wild-type strain *Bacillus subtilis* 168. Since the upstream sequence of menF existing in the fused segment was genetically homologous to the upstream sequence of menF on the chromosome of *Bacillus subtilis* 168, and the menF gene existing in the fused segment was genetically homologous to the menF gene on the chromosome of *Bacillus subtilis* 168, through homologous recombination, the natural promoter of the menF gene on the chromosome of *Bacillus subtilis* 168 was replaced with the bleomycin resistance gene zeo and the $P_{43}$ promoter in the fused segment. The specific steps were as follows:

I. The fused segment constructed in step (2) was electro-transformed into competent cells of *Bacillus subtilis* 168, and the amount of the fused segment added was 100-300 ng. The electro-transformation conditions were as follows: the voltage was 2.5 kV, the electric shock time was 5 ms, resuscitation was performed at 37° C. for 5 h, the *Bacillus subtilis* 168 was spread on a bleomycin-resistant LB plate with a final concentration of 10 μg/mL, and anaerobic culture was performed at 37° C. for 48 h. The *Bacillus subtilis* positive in bleomycin resistance was successfully transformed.

II. The single colony growing on the plate was selected, and primers BS1 YZ.FOR and BS1 YZ.REV were used for verifying the colony by PCR. After replacement, the amplified segment length was 1,350 bp (see FIG. 1). Sequencing was performed, and if the sequence was correct, the natural promoter of the menF gene on the chromosome of *Bacillus subtilis* 168 was successfully replaced with the lox71-zeo-lox66-$P_{43}$ fused gene. Finally, through a Cre/lox recombination system, the bleomycin resistance gene zeo was knocked out, and finally a strain *Bacillus subtilis* 168, $P_{43}$-menF was obtained, named BS1.

TABLE 3

Primer sequence list

| Primer | Sequence (5'-3') | No. |
|---|---|---|
| menF-up.FOR | GCATTCATCGTCATATCATCATAGCTGAGC | SEQ ID NO. 7 |
| menF-up.REV | TGTGAAATTGTTATCCGCTCGAGACATTCCT CCATAATCCTTAAAATGCTTTTAATACC | SEQ ID NO. 8 |
| $P_{43}$.For | TGATAGGTGGTATGTTTTCGCTTGAAC | SEQ ID NO. 9 |
| $P_{43}$.Rev | GTGTACATTCCTCTCTTACCTATAATGG | SEQ ID NO. 10 |
| menF.FOR | TTTAAGGATTATGGAGGAATGTCTCGAGCG GATAACAATTTCACACAGGAAAC | SEQ ID NO. 11 |
| menF.REV | AATCATACCTACCACAATATCATGCTCAAG | SEQ ID NO. 12 |
| BS1 YZ.For | TTCCATATCCTGCGGCGTTTGT | SEQ ID NO. 13 |
| BS1 YZ.Rev | ACGAAGTTATTCAGTCCTGCTCCTC | SEQ ID NO. 14 |

Example 2: Construction of Recombinant Strain BS2

On the basis of the strain BS1 obtained in Example 1, by using the method similar to that in Example 1, the natural promoter of the dihydroxynaphthoic acid synthetase (menB, genebank ID: 937195) gene on the chromosome of *Bacillus subtilis* 168 was replaced with a $P_{43}$ promoter. The specific construction process was as follows:

(1) Obtaining of Fused Segment

The genome of *Bacillus subtilis* 168 was used as a template, and the upstream homologous arm sequence menB-up and the menB gene segment of the menB gene, and the $P_{43}$ promoter sequence were amplified separately. A lox71-zeo-lox66 cassette sequence (with the sequence shown in SEQ ID NO. 2) was artificially synthesized. Then overlap extension PCR was performed on the four segments: the menB-up, the lox71-zeo-lox66 cassette, the $P_{43}$ promoter sequence, and the menB gene segment to obtain a fused gene segment menB$_{up}$-lox71-zeo-lox66-$P_{43}$-menB.

(2) Homologous Recombination

The fused segment obtained in step (1) was transformed into the competent cells of BS1, and the BS1 was spread on a bleomycin-resistant LB plate. The single colony growing on the plate was selected, and PCR verification and sequencing were performed on the colony. Finally, through the Cre/lox recombination system, the bleomycin resistance gene zeo in the strain was knocked out, and finally a *Bacillus subtilis* 168, $P_{43}$-menF $P_{43}$-menB was obtained, named BS2.

Example 3: Construction of Recombinant Strain BS3

On the basis of the strain BS2 obtained in Example 2, by using the method similar to that in Example 1, the natural promoter of an O-succinylbenzoic acid-CoA ligase (menE, genebank ID: 937132) gene in *Bacillus subtilis* was replaced with a $P_{hbs}$ promoter (with the sequence shown in SEQ ID NO. 5). The specific construction process was as follows:

(1) Obtaining of Fused Segment

The genome of *Bacillus subtilis* 168 was used as a template, and the upstream homologous arm sequence menE-up and the menE gene segment of the menE gene, and the $P_{hbs}$ promoter sequence were amplified separately. A lox71-zeo-lox66 cassette sequence (with the sequence shown in SEQ ID NO. 2) was artificially synthesized. Then overlap extension PCR was performed on the four segments: the menE-up, the lox71-zeo-lox66 cassette, the $P_{hbs}$ promoter sequence, and the menE gene segment to obtain a fused gene segment menE$_{up}$-lox71-zeo-lox66-$P_{hbs}$-menE.

(2) Homologous Recombination

The fused segment obtained in step (1) was transformed into the competent cells of BS2. Then, through the Cre/lox recombination system, the bleomycin resistance gene zeo in the strain was knocked out to obtain a strain *Bacillus subtilis* 168, $P_{43}$-menF $P_{43}$-menB $P_{hbs}$-menE, named BS3.

Example 4: Construction of Recombinant Strain BS4

On the basis of the strain BS3 obtained in Example 3, by using the method similar to that in Example 1, an isochorismatase (siderophore specific) (dhbB, genebank ID: 936582) gene on the chromosome of *Bacillus subtilis* was replaced with an isochorismate synthase (entC, genebank ID: 945511) gene derived from *E. coli* K12 and containing a $P_{43}$ promotor. The specific construction process was as follows:

(1) Obtaining of Fused Segment

The genome of *Bacillus subtilis* 168 was used as a template, and the upstream homologous arm sequence dhbB-up of the dhbB gene, the downstream homologous arm sequence dhbB-down of the dhbB and the $P_{43}$ promoter sequence were amplified separately. A lox71-zeo-lox66 cassette sequence (with the sequence shown in SEQ ID NO. 2) was artificially synthesized. The genome of *E. coli* K12 was used as a template, and the entC gene sequence was amplified. Then overlap extension PCR was performed on the five segments: the dhbB-up, the lox71-zeo-lox66 cassette, the $P_{43}$ promoter sequence, the entC gene sequence, and the dhbB-down gene segment to obtain a fused gene segment dhbB$_{up}$-lox71-zeo-lox66-$P_{43}$-entC-dhbB$_{down}$.

(2) Homologous Recombination

The fused segment obtained in step (1) was transformed into the competent cells of BS3. Then, through the Cre/lox recombination system, the bleomycin resistance gene zeo in the strain was knocked out to obtain a strain *Bacillus subtilis* 168, $P_{43}$-menF $P_{43}$-menB $P_{hbs}$-menE $P_{43}$-entC ΔdhbB, named BS4.

Example 5: Construction of Recombinant Strain BS5

On the basis of the strain BS4 obtained in Example 4, by using the method similar to that in Example 1, the natural promoter of a transketolase (tkt, genebank ID: 937377) gene on the chromosome of *Bacillus subtilis* was replaced with a $P_{hbs}$ promoter. The specific construction process was as follows:

(1) Obtaining of Fused Segment

The genome of *Bacillus subtilis* 168 was used as a template, and the upstream homologous arm sequence tkt-up and the tkt gene segment of the tkt gene, and the $P_{hbs}$ promoter sequence were amplified separately. A lox71-zeo-lox66 cassette sequence (with the sequence shown in SEQ ID NO. 2) was artificially synthesized. Then overlap extension PCR was performed on the four segments: the tkt-up, the lox71-zeo-lox66 cassette, the $P_{hbs}$ promoter sequence, and the tkt gene segment to obtain a fused gene segment tkt$_{up}$-lox71-zeo-lox66-$P_{hbs}$-tkt.

(2) Homologous Recombination

The fused segment obtained in step (1) was transformed into the competent cells of BS4. Then, through the Cre/lox recombination system, the bleomycin resistance gene zeo in the strain was knocked out to finally obtain a strain *Bacillus subtilis* 168, $P_{43}$-menF $P_{43}$-menB $P_{hbs}$-menE $P_{43}$-entC ΔdhbB $P_{hbs}$-tkt, named BS5.

Example 6: Construction of Recombinant Strain BS6

On the basis of the strain BS5 obtained in Example 5, by using the method similar to that in Example 1, a phosphoenolpyruvate synthetase (ppsA, genebank ID: 946209) gene derived from *E. coli* K12 and containing a $P_{43}$ promotor was integrated between an N-acetylmuramic acid deacetylase (yjeA, genebank ID: 936440) gene and a yjfA (genebank ID: 939830) gene on the chromosome of *Bacillus subtilis*, and a phosphotransferase system (PTS) glucose-specific enzyme IICBA component (ptsG, genebank ID: 939255) gene on the chromosome was knocked out. The specific construction process was as follows:

(1) Obtaining of Fused Segment

The genome of *E. coli* K12 was used as a template, and the ppsA gene was amplified. The genome of *Bacillus subtilis* 168 was used as a template, and the yjeA gene, the yjfA gene and the $P_{43}$ promoter sequence were amplified separately. A lox71-zeo-lox66 cassette sequence (with the sequence shown in SEQ ID NO. 2) was artificially synthesized. Then overlap extension PCR was performed on the five segments: the yjeA, the lox71-zeo-lox66 cassette, the $P_{43}$, the ppsA, and the yjfA to obtain a fused gene segment yjeA-lox71-zeo-lox66-$P_{43}$-ppsA-yjfA.

The genome of *Bacillus subtilis* 168 was used as a template, and the upstream homologous arm ptsG-up and downstream homologous arm ptsG-down of the ptsG were amplified separately. Overlap extension PCR was performed on the ptsG-up, the lox71-zeo-lox66 and the ptsG-down to obtain a fused gene segment ptsG$_{up}$-lox71-zeo-lox66-ptsG$_{down}$.

(2) Homologous Recombination

The fused segments yjeA-lox71-zeo-lox66-$P_{43}$-ppsA-yjfA and ptsG$_{up}$-lox71-zeo-lox66-ptsG$_{down}$ obtained in step (1) were both transformed into the competent cells of BS5. Then, through the Cre/lox recombination system, the bleomycin resistance gene zeo in the strain was knocked out to finally obtain *Bacillus subtilis* 168 $P_{43}$-menF $P_{43}$-menB $P_{hbs}$-menE $P_{43}$-entC ΔdhbB $P_{hbs}$-tkt $P_{43}$-ppsA ΔptsG, named BS6.

Example 7: Construction of Recombinant Strain BS7

On the basis of the strain BS6 obtained in Example 6, by using the method similar to that in Example 1, an artificially synthetic aroG$^{fbr}$ gene (with the sequence shown in SEQ ID NO. 6) was fused with a promotor $P_{hbs}$ and then integrated between a stress protein (ytxj, genebank ID: 937308) gene and a 3-deoxy-D-arabino-heptulosonate 7-phosphate synthase (aroA, genebank ID: 937853) gene on the genome of *Bacillus subtilis*. The specific construction process was as follows:

(1) Obtaining of Fused Segment

An aroG$^{fbr}$ gene (with the sequence shown in SEQ ID NO. 6) was artificially synthesized. The genome of *Bacillus subtilis* 168 was used as a template, and a ytxj gene, an aroA gene and the $P_{hbs}$ promoter sequence were amplified separately. Then overlap extension PCR was performed on the five segments: the ytxj, the lox71-zeo-lox66, the $P_{hbs}$, the aroG$^{fbr}$ and the aroA to obtain a fused gene segment ytxj-lox71-zeo-lox66-$P_{hbs}$-aroG$^{fbr}$-aroA.

(2) Homologous Recombination

The fused segment obtained in step (1) was transformed into the competent cells of BS6. Then, through the Cre/lox recombination system, the bleomycin resistance gene zeo in the strain was knocked out to finally construct a strain *Bacillus subtilis* 168 $P_{43}$-menF $P_{43}$-menB $P_{hbs}$-menE $P_{43}$-entC ΔdhbB $P_{hbs}$-tkt $P_{43}$-ppsA ΔptsG $P_{hbs}$-aroG$^{fbr}$, named BS7.

Example 8: Construction of Recombinant Strain BS8

On the basis of the strain BS7 obtained in Example 7, by using the method similar to that in Example 1, the natural promoter of a shikimate kinase (aroK, genebank ID: 938343) gene on the chromosome of *Bacillus subtilis* was replaced with a $P_{43}$ promoter. The specific construction process was as follows:

(1) Obtaining of Fused Segment

The genome of *Bacillus subtilis* 168 was used as a template, and the upstream homologous arm sequence aroK-up and the aroK gene segment of the aroK gene, and the $P_{43}$ promoter sequence were amplified separately. A lox71-zeo-lox66 cassette sequence (with the sequence shown in SEQ ID NO.2) was artificially synthesized. Then overlap extension PCR was performed on the four segments: the aroK-up, the lox71-zeo-lox66 cassette, the $P_{43}$ promotor sequence and the aroK gene segment to obtain a fused gene segment aroK$_{up}$-lox71-zeo-lox66-$P_{43}$-aroK.

(2) Homologous Recombination

The fused segment obtained in step (1) was transformed into the competent cells of BS7. Then, through the Cre/lox recombination system, the bleomycin resistance gene zeo in the strain was knocked out to finally construct a strain *Bacillus subtilis* 168 $P_{43}$-menF $P_{43}$-menB $P_{hbs}$-menE $P_{43}$-entC ΔdhbB $P_{hbs}$-tkt $P_{43}$-ppsA ΔptsG $P_{hbs}$-aroG$^{fbr}$ $P_{43}$-aroK, named BS8.

Example 9: Construction of Recombinant Strain BS9

On the basis of the strain BS8 obtained in Example 8, by using the method similar to that in Example 1, the natural promoter of a farnesyl diphosphate synthase (ispA, genebank ID: 938652) gene on the chromosome of *Bacillus subtilis* was replaced with a $P_{hbs}$ promoter. The specific construction process was as follows:
(1) Obtaining of Fused Segment The genome of *Bacillus subtilis* 168 was used as a template, and the upstream homologous arm sequence ispA-up and the ispA gene segment of the ispA gene, and the $P_{hbs}$ promoter sequence were amplified separately. A lox71-zeo-lox66 cassette sequence (with the sequence shown in SEQ ID NO. 2) was artificially synthesized. Then overlap extension PCR was performed on the four segments: the ispA-up, the lox71-zeo-lox66 cassette, the $P_{hbs}$ promoter sequence, and the ispA gene segment to obtain a fused gene segment ispA$_{up}$-lox71-zeo-lox66-$P_{hbs}$-ispA.
(2) Homologous Recombination The fused segment obtained in step (1) was transformed into the competent cells of BS8. Then, through the Cre/lox recombination system, the bleomycin resistance gene zeo in the strain was knocked out to finally construct a strain *Bacillus subtilis* 168 $P_{43}$-menF $P_{43}$-menB $P_{hbs}$-menE $P_{43}$-entC ΔdhbB $P_{hbs}$-tkt $P_{43}$-ppsA ΔptsG $P_{hbs}$-aroG$^{fbr}$$P_{43}$-aroK $P_{hbs}$-ispA, named BS9.

Example 10: Construction of Recombinant Strain BS10

On the basis of the strain BS9 obtained in Example 9, by using the method similar to that in Example 1, the natural promoter of a heptaprenyl diphosphate synthase component I (hepS/T, genebank ID: 938998) gene on the chromosome of *Bacillus subtilis* was replaced with a $P_{43}$ promoter. The specific construction process was as follows:
(1) Obtaining of Fused Segment The genome of *Bacillus subtilis* 168 was used as a template, and the upstream homologous arm sequence hepS/T-up and the hepS/T gene segment of the hepS/T gene, and the $P_{43}$ promoter sequence were amplified separately. A lox71-zeo-lox66 cassette sequence (with the sequence shown in SEQ ID NO. 2) was artificially synthesized. Then overlap extension PCR was performed on the four segments: the hepS/T-up, the lox71-zeo-lox66 cassette, the $P_{43}$ promoter sequence, and the hepS/T gene segment to obtain a fused gene segment hepS/T$_{up}$-lox71-zeo-lox66-$P_{43}$-hepS/T.
(2) Homologous Recombination The fused segment obtained in step (1) was transformed into the competent cells of BS9. Then, through the Cre/lox recombination system, the bleomycin resistance gene zeo in the strain was knocked out to finally construct a strain *Bacillus subtilis* 168 $P_{43}$-menF $P_{43}$-menB $P_{hbs}$-menE $P_{43}$-entC ΔdhbB $P_{hbs}$-tkt $P_{43}$-ppsA ΔptsG $P_{hbs}$-aroG$^{fbr}$$P_{43}$-aroK $P_{hbs}$-ispA $P_{43}$-hepS/T, named BS10.

Example 11: Construction of Recombinant Strain BS11

On the basis of the strain BS10 obtained in Example 10, by using the method similar to that in Example 1, a 2-dehydro-3-deoxy-phosphogluconate aldolase (kdpG, genebank ID: 33073472) gene derived from *Zymomonas mobilis* was fused with a promoter $P_{hbs}$ and then integrated between a putative uronase (yclG, genebank ID: 938292) gene and a spore germination receptor subunit (gerkA, genebank ID: 938285) gene on the chromosome of *Bacillus subtilis*. The specific construction process was as follows:
(1) Obtaining of Fused Segment The genome of *Zymomonas mobilis* was used as a template to synthesize a kdpG gene. The genome of *Bacillus subtilis* 168 was used as a template, and a yclG gene, a $P_{hbs}$ promotor sequence and a gerkA gene were amplified separately. A lox71-zeo-lox66 cassette sequence (with the sequence shown in SEQ ID NO. 2) was artificially synthesized. Then overlap extension PCR was performed on the five segments: the yclG, the lox71-zeo-lox66 cassette, the $P_{hbs}$ promoter sequence, the kdpG, and the gerkA to obtain a fused gene segment yclG-lox71-zeo-lox66-$P_{hbs}$-kdpG-gerkA.
(2) Homologous Recombination The fused segment obtained in step (1) was transformed into the competent cells of BS10. Then, through the Cre/lox recombination system, the bleomycin resistance gene zeo in the strain was knocked out to finally construct a strain *Bacillus subtilis* 168 $P_{43}$-menF $P_{43}$-menB $P_{hbs}$-menE $P_{43}$-entC ΔdhbB $P_{hbs}$-tkt $P_{43}$-ppsA ΔptsG $P_{hbs}$-aroG$^{fbr}$::lox72 $P_{43}$-aroK $P_{hbs}$-ispA $P_{43}$-hepS/T $P_{hbs}$-kdpG, named BS11.

Example 12: Construction of Recombinant Strain BS12

On the basis of the strain BS11 obtained in Example 11, by using the method similar to that in Example 1, the natural promoter of a 1-deoxy-D-xylulose-5-phosphate reductoisomerase (dxr, genebank ID: 939636) gene on the chromosome of *Bacillus subtilis* was replaced with a $P_{43}$ promoter. The specific construction process was as follows:
(1) Obtaining of Fused Segment The genome of *Bacillus subtilis* 168 was used as a template, and the upstream homologous arm sequence dxr-up and the dxr gene segment of the dxr gene, and the $P_{43}$ promoter sequence are amplified separately. A lox71-zeo-lox66 cassette sequence (with the sequence shown in SEQ ID NO. 2) was artificially synthesized. Then overlap extension PCR was performed on the four segments: the dxr-up, the lox71-zeo-lox66 cassette, the $P_{43}$ promoter sequence, and the dxr gene segment to obtain a fused gene segment dxr$_{up}$-lox71-zeo-lox66-$P_{43}$-dxr.
(2) Homologous Recombination The fused segment obtained in step (1) was transformed into the competent cells of BS11. Then, through the Cre/lox recombination system, the bleomycin resistance gene zeo in the strain was knocked out to obtain a strain *Bacillus subtilis* 168 $P_{43}$-menF $P_{43}$-menB $P_{hbs}$-menE $P_{43}$-entC ΔdhbB $P_{hbs}$-tkt $P_{43}$-ppsA ΔptsG $P_{hbs}$-aroG$^{fbr}$ $P_{43}$-aroK $P_{hbs}$-ispA $P_{43}$-hepS/T $P_{hbs}$-kdpG $P_{43}$-dxr, named BS12.

Example 13: Construction of Recombinant Strain BS13

On the basis of the strain BS12 obtained in Example 12, by using the method similar to that in Example 1, the natural promoter of a 1-deoxyxylulose-5-phosphate synthase (dxs, genebank ID: 938609) gene in *Bacillus subtilis* 168 was replaced with a $P_{43}$ promoter. The specific construction process was as follows:

(1) Obtaining of Fused Segment

The genome of *Bacillus subtilis* 168 was used as a template, and the upstream homologous arm sequence dxs-up and the dxs gene segment of the dxs gene, and the $P_{43}$ promoter sequence are amplified separately. A lox71-zeo-lox66 cassette sequence (with the sequence shown in SEQ ID NO. 2) was artificially synthesized. Then overlap extension PCR was performed on the four segments: the dxs-up, the lox71-zeo-lox66 cassette, the $P_{43}$ promoter sequence, and the dxs gene segment to obtain a fused gene segment $dxs_{up}$-lox71-zeo-lox66-$P_{43}$-dxs.

(2) Homologous Recombination

The fused segment obtained in step (1) was transformed into the competent cells of BS12. Then, through the Cre/lox recombination system, the bleomycin resistance gene zeo in the strain was knocked out to obtain a strain *Bacillus subtilis* 168 $P_{43}$-menF $P_{43}$-menB $P_{hbs}$-menE $P_{43}$-entC ΔdhbB $P_{hbs}$-tkt $P_{43}$-ppsA ΔptsG $P_{hbs}$-aroG$^{fbr}$ $P_{43}$-aroK $P_{hbs}$-ispA $P_{43}$-hepS/T $P_{hbs}$-kdpG $P_{43}$-dxr $P_{43}$-dxs, named BS13.

Example 14: Construction of Recombinant Strain BS14

On the basis of the strain BS13 obtained in Example 13, by using the method similar to that in Example 1, the natural promoter of an isopentenyl diphosphate isomerase (typeII) (fni, genebank ID: 938985) gene on the chromosome of *Bacillus subtilis* was replaced with a $P_{43}$ promoter. The specific construction process was as follows:

(1) Obtaining of Fused Segment

The genome of *Bacillus subtilis* 168 was used as a template, and the upstream homologous arm sequence fni-up and the fni gene segment of the fni gene, and the $P_{43}$ promoter sequence are amplified separately. A lox71-zeo-lox66 cassette sequence (with the sequence shown in SEQ ID NO. 2) was artificially synthesized. Then overlap extension PCR was performed on the four segments: the fni-up, the lox71-zeo-lox66 cassette, the $P_{43}$ promoter sequence, and the fni gene segment to obtain a fused gene segment $fni_{up}$-lox71-zeo-lox66-$P_{43}$-fni.

(2) Homologous Recombination

The fused segment obtained in step (1) was transformed into the competent cells of BS13. Then, through the Cre/lox recombination system, the bleomycin resistance gene zeo in the strain was knocked out to construct a strain *Bacillus subtilis* 168 $P_{43}$-menF $P_{43}$-menB $P_{hbs}$-menE $P_{43}$-entC ΔdhbB $P_{hbs}$-tkt $P_{43}$-ppsA ΔptsG $P_{hbs}$-aroG$^{fbr}$ $P_{43}$-aroK $P_{hbs}$-ispA $P_{43}$-hepS/T $P_{hbs}$-kdpG $P_{43}$-dxr $P_{43}$-dxs $P_{43}$-fni, named BS14.

Example 15: Production of MK-7 by Strain Fermentation

Formula of a seed medium (in mass percentage): tryptone 1%, yeast extract 0.5%, and sodium chloride 1%.

Formula of a fermentation medium (in mass percentage): soy peptone 5%, glucose 5%, sucrose 5%, and $KH_2PO_3$ 0.06%.

(1) Preparation of Seed Solution

The seed medium was inoculated with the wild-type strain *Bacillus subtilis* 168 and the recombinant strains BS1-14 constructed in Examples 1-14 were respectively, and culturing was performed at 37° C. and 220 rpm for 12 h to obtain the *Bacillus subtilis* seed solutions.

(2) Fermentation Culture

The seed solutions obtained in step (1) were transferred to the fermentation medium at an inoculum concentration of 15%. After 6 days of culture at 41° C. and 220 rpm, the fermentation broth was taken to determine the content of MK-7 (see Table 4).

TABLE 4

Production of MK-7 by strain fermentation

| Strain | Yield of MK-7 (mg/L) | Relative content of MK-7 |
|---|---|---|
| BS168 (Original strain) | 9.5 | 1 |
| BS1 | 9.1 | 0.96 |
| BS2 | 9.5 | 1 |
| BS3 | 9.2 | 0.97 |
| BS4 | 9.6 | 1.01 |
| BS5 | 9.2 | 0.97 |
| BS6 | 15.1 | 1.59 |
| BS7 | 16.2 | 1.71 |
| BS8 | 17.4 | 1.83 |
| BS9 | 19.6 | 2.06 |
| BS10 | 21.2 | 2.23 |
| BS11 | 24.2 | 2.55 |
| BS12 | 26.4 | 2.78 |
| BS13 | 28.2 | 2.97 |
| BS14 | 33.5 | 3.53 |

Although the present disclosure has been disclosed as above in preferred examples, it is not intended to limit the present disclosure. Anyone in this art can make various changes and modifications without departing from the spirit and scope of the present disclosure. Therefore, the protection scope of the present disclosure should be defined by the claims.

What is claimed is:

1. A recombinant *Bacillus subtilis* for increasing the yield of menaquinone 7, wherein *Bacillus subtilis* 168 is taken as an original strain; natural promoters of a menaquinone-specific isochorismate synthase gene menF and a dihydroxynaphthoic acid synthetase gene menB on a chromosome are replaced with $P_{43}$ promoters; natural promoters of an O-succinylbenzoic acid-CoA ligase gene menE and a transketolase gene tkt on the chromosome are replaced with $P_{hbs}$ promoters; expression of an exogenous isochorismate synthase gene entC and an exogenous phosphoenolpyruvate synthetase gene ppsA on the chromosome are enhanced with $P_{43}$ promoters, and a phosphotransferase system (PTS) glucose-specific enzyme IICBA component gene ptsG on the chromosome is knocked out; the sequence of the $P_{43}$ promoter is shown in SEQ ID NO: 3; and the sequence of the $P_{hbs}$ promoter is shown in SEQ ID NO: 5.

2. The recombinant *Bacillus subtilis* according to claim 1, wherein the sequence of the menF gene is shown in SEQ ID NO: 4; the sequence of the menB gene is shown in SEQ ID NO: 15; the sequence of the menE gene is shown in SEQ ID NO: 16; the sequence of the tkt gene is shown in SEQ ID NO: 17; the sequence of the entC gene is shown in SEQ ID NO: 18; the sequence of the ppsA gene is shown in SEQ ID NO: 19; and the sequence of the ptsG gene is shown in SEQ ID NO: 20.

3. The recombinant *Bacillus subtilis* according to claim 1, wherein expression of an exogenous aroG$^{fbr}$ gene on the chromosome is enhanced with the $P_{hbs}$ promoter; and the sequence of the aroG$^{fbr}$ gene is shown in SEQ ID NO: 6.

4. The recombinant *Bacillus subtilis* according to claim 3, wherein natural promoter of a shikimate kinase gene aroK on the chromosome is replaced with the $P_{43}$ promoter.

5. The recombinant *Bacillus subtilis* according to claim 4, wherein natural promoter of a farnesyl diphosphate synthase gene ispA on the chromosome of *Bacillus subtilis* is replaced with the $P_{hbs}$ promoter.

6. The recombinant *Bacillus subtilis* according to claim 5, wherein natural promoter of a heptaprenyl diphosphate synthase component I (hepS/T, SEQ ID NO: 21) gene on the chromosome of *Bacillus subtilis* is replaced with the $P_{43}$ promoter.

7. The recombinant *Bacillus subtilis* according to claim 6, wherein expression of an exogenous 2-dehydro-3-deoxy-phosphogluconate aldolase gene kdpG on the chromosome is enhanced with the $P_{hbs}$ promoter.

8. The recombinant *Bacillus subtilis* according to claim 7, wherein natural promoter of a 1-deoxy-D-xylulose-5-phosphate reductoisomerase gene dxr on the chromosome of *Bacillus subtilis* is replaced with the $P_{43}$ promoter.

9. The recombinant *Bacillus subtilis* according to claim 8, wherein natural promoter of a 1-deoxyxylulose-5-phosphate synthase gene dxs on the chromosome is replaced with the $P_{43}$ promoter.

10. The recombinant *Bacillus subtilis* according to claim 9, wherein natural promoter of a gene in an isopentenyl diphosphate isomerase (type II) (fni, SEQ ID NO: 22) on the chromosome of *Bacillus subtilis* is replaced with the $P_{43}$ promoter.

* * * * *

SEQUENCE LISTING

<160> NUMBER OF SEQ ID NOS: 22

<210> SEQ ID NO 1
<211> LENGTH: 846
<212> TYPE: DNA
<213> ORGANISM: Bacillus subtilis 168

<400> SEQUENCE: 1
gcattcatcg tcatatcatc atagctgagc ggagggtttt ccatatcctg cggcgtttgt    60
gagttcccat atttttcgac atcctgatag gaatcctcac tgtcatatgg cgctctgatt    120

```
tcttcatcat catcaaattc aaattgcccg aatggtgttt cttcttcaat cggacggtct    180
ttggaaacca cgtcctgtga cgaatactcc gcgagggttg tggcagtcgg aagcgcttca    240
agtcgttcga aagggatttc ctttccgctg acttcacaaa tgccatacgt accgttttct    300
atcgccttca atgaatgctc aatgtcccga aggtgctctc tctcatgcaa gtctagagcg    360
atgtctttct cacgctcgta aagttctgtc gcctgatcgc cgggatggtt gtcgtatgcc    420
gaaagctcac cccacgaatc ataaggaaag gctgagttaa gctgaaaatg atcattgtct    480
ttgaaacggt ttaagatatc ttttttcgtt tgttccagtt catttttaa atgctgaagc     540 tgttctttcg taagcaatgt gatcgcctcg tttctgtgtg atgcatacct ttagtatgaa    600
cagatcgcct gagaactttc ataaatggcg ggtggaggaa tataggaggt tttcctttta    660
tggtaagcgg atacaacctt tgctatcagt ggagaaagaa atttaagctt tgtttctttt    720
tcatttctga aattaggttt ataataggta aggcaggcca tttggactgc atgatctgtg    780
tttgacacaa aggagacaca ggtgtatggt attaaaagca ttttaaggat tatggaggaa    840
tgtctc                                                               846

<210> SEQ ID NO 2
<211> LENGTH: 588
<212> TYPE: DNA
<213> ORGANISM: Artificial Sequence
<220> FEATURE:
<223> OTHER INFORMATION: Synthesized lox71-zeo-lox66 cassette

<400> SEQUENCE: 2
gagcggataa caatttcaca caggaaacag ctatgaccat gattacgaat tcgagctcgg     60
tacccgggga tcctctagag ataccgttcg tatagcatac attatacgaa gttatcttga    120
tatggctttt tatatgtgtt actctacata cagaaaggag gaactaaaca tggccaagtt    180
gaccagtgcc gttccggtgc tcaccgcgcg cgacgtcgcc ggagcggtcg agttctggac    240
cgaccggctc gggttctccc gggacttcgt ggaggacgac ttcgccggtg tggtccggga    300
cgacgtgacc ctgttcatca gcgcggtcca ggaccaggtg gtgccggaca cacccctggc    360
ctgggtgtgg gtgcgcggcc tggacagagct gtacgccgag tggtcggagg tcgtgtccac    420
gaacttccgg gacgcctccg gccggccat gaccgagatc ggcgagcagc cgtggggcg    480 ggagttcgcc ctgcgcgacc cggccggcaa ctgcgtgcac ttcgtggccg aggagcagga    540
ctgaataact tcgtatagca tacattatac gaacggtaaa tcgtcgac                588

<210> SEQ ID NO 3
<211> LENGTH: 300
<212> TYPE: DNA
<213> ORGANISM: Bacillus subtilis 168

<400> SEQUENCE: 3
tgataggtgg tatgttttcg cttgaacttt taaatacagc cattgaacat acggttgatt     60
taataactga caaacatcac cctcttgcta aagcggccaa ggacgctgcc gccggggctg    120
tttgcgtttt tgccgtgatt tcgtgtatca ttggtttact tatttttttg ccaaagctgt    180
aatggctgaa aattcttaca tttatttttac attttttagaa atgggcgtga aaaaaagcgc    240
gcgattatgt aaaatataaa gtgatagcgg taccattata ggtaagagag gaatgtacac    300

<210> SEQ ID NO 4
<211> LENGTH: 847
<212> TYPE: DNA
<213> ORGANISM: Bacillus subtilis 168
```

<400> SEQUENCE: 4

```
atggtgacaa cggtgcagcg tacgttccga aaggaagttc tacatgcatt acataaagcc    60
aaagaagtca accatgctgt cttaataagc tattcgagac aaatcgagtc tcttgaccct   120
ctatcatttt tcaattacgg agcaaaaaaa tatacaggca atcgattttt ttggtcagat   180
cctgaaagtg aattgacaat agtcggtctt ggcaagaag cggttttcca gacaaatcaa   240
aaaaacagcg agcggtatcg tgaggttttt gaacaatggg agcgctttaa aaagacggct   300
tttcatatt atgaagaaga aaagctgcag cattctgcag tgggacctgt gttattcgga   360
ggattttctt tgaccccttg cgaagaaaga ggttcacaat gggaccattt ctcggaaggg   420
gatttctttg tgcctgcgct tatgctgacg atgactgctg aaggcccgtt cttaacagtt   480
aacagatggg taagcggagg agaagacgca gaagctgttt tagaaggctt aaaagctttt   540
gcggcggaat ttatggttcc cgatttcaag caagaagatc aggctgtgat tgcagcagcc   600
gaaagagctgg ataaggatga ttggctgaaa gcaatcgaaa cggccacaag ccaaattaaa   660
gagaaacaat atgataaggt tgttcttgcc cgagagctgc tgctcacgtt tgacggtcca   720
atccaaattg aaccggtgct taaaacgctt ctggacgatc agcagacaag ctatgttttt   780
gcaattgaac aagaaggcaa aacctttgtc ggcgcgtctc cggaaagact gatcaaaaga   840
gacggcg                                                              847
```

<210> SEQ ID NO 5
<211> LENGTH: 328
<212> TYPE: DNA
<213> ORGANISM: Bacillus subtilis 168

<400> SEQUENCE: 5

```
cttaataatg gaaaaggatc aaggaatagg atgaaaaaag gaaaaaaagg aatattcgtt    60
cggtaaatca ccttaaatcc ttgacgagca agggattgac gctttaaaat gcttgatatg   120
gcttttata tgtgttactc tacatacaga aattcttcac tttgttggac aaacattcct   180
cagagtgcag ttttcttaa aaagccgttt aattgtcttt ctcttacttg ctctcatttt   240
tttctgagac aggtttagaa tcagactgaa ctgtgaagaa atgataataa acgaactgaa   300
tgtatccttt tgggaggagg tgaaaggc                                      328
```

<210> SEQ ID NO 6
<211> LENGTH: 1053
<212> TYPE: DNA
<213> ORGANISM: Artificial Sequence
<220> FEATURE:
<223> OTHER INFORMATION: Synthesized aroGfbr gene

<400> SEQUENCE: 6

```
atgaattatc agaacgacga tttacgcatc aaagaaatca agagttact tcctcctgtc    60
gcattgctgg aaaaattccc cgctactgaa atgccgcga atacggttgc ccatgcccga   120
aaagcgatcc ataagatcct gaaaggtaat gatgatcgcc tgttggttgt gattggccca   180
tgctcaattc atgatcctgt cgcggcaaaa gagtatgcca ctcgcttgct ggcgctgcgt   240
gaagagctga aagatgagct ggaaatcgta atgcgcgtct atttcgaaaa gccgcgtacc   300
acggtgggct ggaaagggct gattaacgat ccgcatatgg ataatagctt ccagatcaac   360
gacggtctgc gtatagcccg taattgctgt cttgatatta cgacagcgg tctgccagcg   420
gcaggtgagt ttctcgatat gatcacccctg caatatctcg ctgacctgat gagctggggc   480
```

-continued

```
gcaattggcg cacgtaccac cgaatcgcag gtgcaccgcg aactggcatc agggctttct      540
tgtccggtcg gcttcaaaaa tggcaccgac ggtacgatta aagtggctat cgatgccatt      600
aatgccgccg gtgcgccgca ctgcttcctg tccgtaacga aatgggggca ttcggcgatt      660
gtgaatacca gcggtaacgg cgattgccat atcattctgc gcggcggtaa agagcctaac      720
tacagcgcga agcacgttgc tgaagtgaaa gaagggctga acaaagcagg cctgccagca      780
caggtgatga tcgatttcag ccatgctaac tcgtccaaac aattcaaaaa gcagatggat      840
gtttgtgctg acgtttgcca gcagattgcc ggtggcgaaa aggccattat tggcgtgatg      900
gtggaaagcc atctggtgga aggcaatcag agcctcgaga gcggggagcc gctggcctac      960
ggtaagagca tcaccgatgc ctgcatcggc tgggaagata ccgatgctct gttacgtcaa     1020
ctggcgaatg cagtaaaagc gcgtcgcggg taa                                  1053
```

<210> SEQ ID NO 7
<211> LENGTH: 30
<212> TYPE: DNA
<213> ORGANISM: Artificial Sequence
<220> FEATURE:
<223> OTHER INFORMATION: Synthesized primer for amplification of
      upstream homologous arm sequence menF-up of menF gene

<400> SEQUENCE: 7
gcattcatcg tcatatcatc atagctgagc                                        30

<210> SEQ ID NO 8
<211> LENGTH: 59
<212> TYPE: DNA
<213> ORGANISM: Artificial Sequence
<220> FEATURE:
<223> OTHER INFORMATION: Synthesized primer for amplification of
      upstream homologous arm sequence menF-up of menF gene

<400> SEQUENCE: 8
tgtgaaattg ttatccgctc gagacattcc tccataatcc ttaaaatgct tttaatacc       59

<210> SEQ ID NO 9
<211> LENGTH: 27
<212> TYPE: DNA
<213> ORGANISM: Artificial Sequence
<220> FEATURE:
<223> OTHER INFORMATION: Synthesized primer for amplification of P43
      promoter sequence

<400> SEQUENCE: 9
tgataggtgg tatgttttcg cttgaac                                           27

<210> SEQ ID NO 10
<211> LENGTH: 28
<212> TYPE: DNA
<213> ORGANISM: Artificial Sequence
<220> FEATURE:
<223> OTHER INFORMATION: Synthesized primer for amplification of P43
      promoter sequence

<400> SEQUENCE: 10
gtgtacattc ctctcttacc tataatgg                                          28

<210> SEQ ID NO 11
<211> LENGTH: 53
<212> TYPE: DNA
<213> ORGANISM: Artificial Sequence
<220> FEATURE:
<223> OTHER INFORMATION: Synthesized primer for amplification of menF gene segment

<400> SEQUENCE: 11
tttaaggatt atggaggaat gtctcgagcg gataacaatt tcacacagga aac        53

<210> SEQ ID NO 12
<211> LENGTH: 30
<212> TYPE: DNA
<213> ORGANISM: Artificial Sequence
<220> FEATURE:
<223> OTHER INFORMATION: Synthesized primer for amplification of menF
      gene segment

<400> SEQUENCE: 12
aatcatacct accacaatat catgctcaag                                   30

<210> SEQ ID NO 13
<211> LENGTH: 22
<212> TYPE: DNA
<213> ORGANISM: Artificial Sequence
<220> FEATURE:
<223> OTHER INFORMATION: Synthesized primer for verifying the colony by
      PCR

<400> SEQUENCE: 13
ttccatatcc tgcggcgttt gt                                           22

<210> SEQ ID NO 14
<211> LENGTH: 25
<212> TYPE: DNA
<213> ORGANISM: Artificial Sequence
<220> FEATURE:
<223> OTHER INFORMATION: Synthesized primer for amplification of Phbs
      promoter

<400> SEQUENCE: 14
acgaagttat tcagtcctgc tcctc                                        25

<210> SEQ ID NO 15
<211> LENGTH: 814
<212> TYPE: DNA
<213> ORGANISM: Bacillus subtilis 168

<400> SEQUENCE: 15
atggctgaat ggaaaacaaa acggacatac gatgagatat gtatgaaacg tataatggca    60
ttgcaaaaat aacaatcaac cgacctgagg tacataatgc gtttacccct aaaacggttg   120
ctgaaatgat tgatgcgttt gctgacgcaa gagacgacca aaacgttggg gttatcgtgc   180
ttgccggtga ggggacaaag cattttgttc tggcggagac caaaaagtgc gcggccacgg   240
tggatatgta ggagacgacc agatccctcg tcttaacgta ttggatcttc agcgtttaat   300
ccgcgtcatc ccgaaaccgg ttgttgcgat ggtgtccgga tatgcgatcg gcggaggcca   360
tgtgcttcac atcgtatgtg acttgacaat tgctgcggac aacgcaattt ttggacaaac   420
aggccctaaa gtgggaagct tcgatgcagg ttacggttct ggctacctgg ctcgaattgt   480
aggacataaa aaagcacgtg aaatctggta cctatgccgt cagtacaacg cacaggaagc   540
actggacatg ggtcttgtca acacagtcgt tcctttggaa cagcttgaag aagaaacgat   600
taaatggtgt gaagaaatgc ttgaaaaaag cccgaccgca ctgcgctttc ttaaagctgc   660
gtttaacgcg gacacagacg gacttgctgg aattcagcag tttgcagggg atgctaccct   720
tctttactac acaacagatg aagcaaaaga aggccgtgat tcctttaagg aaaaacgcaa   780

```
acctgatttc ggacagttcc ctcgttttcc gtga                          814
```

<210> SEQ ID NO 16
<211> LENGTH: 1461
<212> TYPE: DNA
<213> ORGANISM: Bacillus subtilis 168

<400> SEQUENCE: 16

```
atgctgacag aacagcccaa ctggctcatg cagcgggcac agctgacacc tgagagaatc    60
gctctcatct atgaagacca aaccgtgaca tttgcagaat tgtttgccgc gtctaaacga   120
atggcggaac agcttgccgc tcattcggtt cggaaagggg atactgcagc tattttgctc   180
caaaaccgtg cagaaatggt atacgctgtt cacgcttgtt ttttgcttgg tgttaaggcg   240
gtgcttttga atacgaagct gtcaacacat gaaaggctgt ttcagctgga ggattcggga   300
tccggctttt tattgacaga ttcaagcttt gagaagaaag aatatgaaca catcgttcaa   360
acgattgatg tggatgaact gatgaaagaa gcagcagagg aaattgagat cgaggcttat   420
atgcaaatgg atgcaacggc aacgctgatg tatacgtcgg gtacgacagg aaagcccaag   480
ggagttcagc aaacgttcgg aaaccattat ttcagtgcgg tgtcgtccgc tcttaatttg   540
ggtataacag aacaagaccg ctggcttatc gcattgccgc tctttcatat cagcggattg   600
tccgcattat ttaaatctgt gatctatgga atgactgtcg tgcttcacca gcgttttttcc  660
gtaagcgatg tgctgcattc tatcaacagg catgaagtga caatgatatc tgcggtgcag   720
actatgctgg ccagtctttt ggaagaaaca aaccgctgcc ctgaatccat cagatgcatt   780
cttctcggcg gcggtcctgc accgctgcca ttgcttgagg aatgccgtga aaaggattc    840
cctgtctttc agtcatatgg aatgacagaa acatgctcgc aaattgttac cctgtcgccg   900
gaattcagca tggaaaagct cggatctgcg gggaaaccgc tgttttcgtg tgaaatcaaa   960
atagagcggg acggacaggt atgtgaaccg tatgaacacg gtgaaatcat ggtcaaaggc  1020
ccgaatgtca tgaaaagcta ttttaaccgg gagagcgcaa acgaagcctc ctttcaaaat  1080
ggctggctga aaacaggtga tcttggttat ttggacaatg aaggcttttt atatgtatta  1140
gacagacgtt cagatctgat catatccggc ggagaaaaca tttatccggc cgaagtggag  1200
tcagtgctgc tttcacaccc cgctgtggcc gaagccgggg tttcaggggc tgaggacaaa  1260
aaatggggga agtgcctca cgcctatctt gtccttcaca agcctgtgag cgcaggagaa   1320
ttgactgact actgcaaaga acgcttggcg aagtataaaa ttccggcaaa attctttgtg  1380
cttgaccgcc tgccgcgcaa tgcgtctaat aagctcttgc gaaatcagct gaaggatgcg  1440
cgtaaaggag aactgctatg a                                            1461
```

<210> SEQ ID NO 17
<211> LENGTH: 2004
<212> TYPE: DNA
<213> ORGANISM: Bacillus subtilis 168

<400> SEQUENCE: 17

```
atggatacaa ttgaaaagaa atcagttgct accattcgca cactgtcaat agacgctatt    60
gaaaaagcaa attctggtca cccagggatg ccgatgggag ccgctccaat ggcatacacg   120
ctgtggacaa aatttatgaa cgtaagtccg gcaaaccctg gctggtttaa ccgtgaccgt   180
tttgttttat ctgctggaca cgggtcagca ctattataca gcatgcttca tttaagcggg   240
tttgatctta gtattgaaga tcttaaggga ttccgccagt ggggcagcaa acaccagga    300
catccggaat tcggacatac tgccggtgtt gatgctacaa caggtccgct tggccaagga   360
```

```
attgccatgg cagtcggtat ggcaattgct gaacgccatt tagcggaaac atacaaccgc      420
gattcattta acgtagtcga tcattataca tacagtattt gcggtgatgg tgatttaatg      480
gaaggtattt cttctgaagc cgcttcactc gcaggccatc ttcagcttgg ccgtctgatc      540
gtactatacg attctaatga catctctctt gatggagacc tcgaccgttc attctctgaa      600
aacgtgaaac agcgttttga agcaatgaat tgggaagttc tttatgttga ggatggaaac      660
aatattgaag aattaacagc ggctatcgaa aaagcacgcc aaaatgaaaa gaaacctaca      720
ttaattgaag tgaaaacgac aatcggattc ggttcaccta accgtgccgg tacatccggt      780
gttcacggtg cgccgcttgg taagaagaa agcaaattaa caaagaagc ttacgcgtgg      840 acatatgaag aagacttcta cgttccgtca aagtttatg agcatttcgc tgtagctgtt      900
aaagaatcag gtgagaaaaa agaacaagaa tggaatgctc aattcgctaa atataaagaa      960
gtttatcctg aacttgctga acagcttgaa ctggcaatca aaggagagct tccgaaggac     1020
tgggatcaag aggttcctgt gtatgaaaaa ggaagcagtt tggcatcccg tgcatcttcc     1080
ggtgaagttc tcaacggact tgcgaaaaaa attcctttct ttgtcggagg ttctgctgac     1140
ctagcgggat cgaacaaaac gactattaaa atgccggtg attttacagc ggttgattac     1200
tcaggcaaaa acttctggtt tggtgtacgt gaatttgcga tgggtgcggc cttaaacggt     1260
atggcgcttc atggcggtct tcgtgtattc ggcggaactt tctttgtctt ctctgattac     1320
ctgcgtcctg cgattcgcct tgcagcgtta atgggccttc ctgtgacata tgtcttcaca     1380
catgacagta ttgcggttgg tgaagacggt ccgacgcacg agcctgttga acagcttgct     1440
tcactccgtg cgatgcctaa cctttctttg atccgtccag cagacggcaa tgagacagca     1500
gcagcatgga agcttgcagt gcaaagcact gaccacccaa cagcgctagt gcttacacgt     1560
caaaaccttc ctaccatcga tcaaacatct gaagaagcat tggcaggagt agaaaaaggt     1620
gcatatgtcg tttctaaatc taaaaacgaa acacctgacg ctcttctcat cgcttccgga     1680
tcagaggtag gtcttgcaat tgaagcgcag gctgaattgg caaaagaaaa tatcgatgtt     1740
tctgttgtca gcatgccttc aatgaccgt tttgagaaac aatctgatga atacaaaaac     1800
gaagtccttc ctgcagatgt gaaaaaacgt cttgcaattg aaatgggctc atcatttgga     1860
tggggcaaat acacggggct tgaaggtgac gttctcggca tagaccgatt cggtgcatct     1920
gctcctggtg aaaccatcat taacgaatac ggcttctcag ttccgaacgt agtgaatcga     1980
gttaaggcat taatcaataa gtaa                                              2004
```

<210> SEQ ID NO 18
<211> LENGTH: 1176
<212> TYPE: DNA
<213> ORGANISM: Bacillus subtilis 168

<400> SEQUENCE: 18

```
atggatacgt cactggctga ggaagtacag cagaccatgg caacacttgc gcccaatcgc       60
tttttcttta tgtcgccgta ccgcagtttt acgacgtcag gatgtttcgc ccgcttcgat      120
gaaccggctg tgaacgggga ttcgcccgac agtccctcc agcaaaaact cgccgcgctg      180
tttgccgatg ccaaagcgca gggcatcaaa atccgtgta tggtcggggc gattcccttc      240
gatccacgtc agccttcgtc gctgtatatt cctgaatcct ggcagtcgtt ctcccgtcag      300
gaaaaacaag cttccgcacg ccgtttcacc cgcagccagt cgctgaatgt ggtggaacgc      360
caggcaattc cggagcaaac cacgtttgaa cagatggttg cccgcgccgc cgcacttacc      420
```

```
gccacgccgc aggtcgacaa agtggtgttg tcacggttga ttgatatcac cactgacgcc    480
gccattgata gtggcgtatt gctggaacgg ttgattgcgc aaaacccggt tagttacaac    540
ttccatgttc cgctggctga tggtggcgtc ctgctggggg ccagcccgga actgctgcta    600
cgtaaagacg gcgagcgttt tagctccatt ccgttagccg gttccgcgcg tcgtcagccg    660
gatgaagtgc tcgatcgcga agcaggtaat cgtctgctgg cgtcagaaaa agatcgccat    720
gaacatgaac tggtgactca ggcgatgaaa gaggtactgc gcgaacgcag tagtgagtta    780
cacgttcctt cttctccaca gctgatcacc acgccgacgc tgtggcatct cgcaactccc    840
tttgaaggta aagcgaattc gcaagaaaac gcactgactc tggcctgtct gctgcatccg    900 accccgcgc tgagcggttt cccgcatcag gccgcgaccc aggttattgc tgaactggaa    960
ccgttcgacc gcgaactgtt tggcggcatt gtgggttggt gtgacagcga aggtaacggc   1020
gaatgggtgg tgaccatccg ctgcgcgaag ctgcgggaaa atcaggtgcg tctgtttgcc   1080
ggagcgggga ttgtgcctgc gtcgtcaccg ttgggtgagt ggcgcgaaac aggcgtcaaa   1140
ctttctacca tgttgaacgt ttttggattg cattaa                             1176

<210> SEQ ID NO 19
<211> LENGTH: 2379
<212> TYPE: DNA
<213> ORGANISM: Bacillus subtilis 168

<400> SEQUENCE: 19
atgtccaaca atggctcgtc accgctggtg ctttggtata accaactcgg catgaatgat     60
gtagacaggg ttgggggcaa aaatgcctcc ctgggtgaaa tgattactaa tctttccgga    120
atgggtgttt ccgttccgaa tggtttcgcc acaaccgccg acgcgtttaa ccagtttctg    180
gaccaaagcg gcgtaaacca gcgcatttat gaactgctgg ataaaacgga tattgacgat    240
gttactcagc ttgcgaaagc gggcgcgcaa atccgccagt ggattatcga cactcccttc    300
cagcctgagc tggaaaacgc catccgcgaa gcctatgcac agctttccgc cgatgacgaa    360
aacgcctctt ttgcggtgcg ctcctccgcc accgcagaag atatgccgga cgcttctttt    420
gccggtcagc aggaaaacctt cctcaacgtt cagggttttg acgccgttct cgtggcagtg    480
aaacatgtat ttgcttctct gtttaacgat cgcgccatct cttatcgtgt gcaccagggt    540
tacgatcacc gtggtgtggc gctctccgcc ggtgttcaac ggatggtgcg ctctgacctc    600
gcatcatctg gcgtgatgtt ctccattgat accgaatccg gctttgacca ggtggtgttt    660
atcacttccg catggggcct tggtgagatg gtcgtgcagg gtgcggttaa cccggatgag    720
ttttacgtgc ataaaccgac actggcggcg aatcgcccgg ctatcgtgcg ccgcaccatg    780
gggtcgaaaa aaatccgcat ggtttacgcg ccgacccagg agcacggcaa gcaggttaaa    840
atcgaagacg taccgcagga acagcgtgac atcttctcgc tgaccaacga agaagtgcag    900
gaactggcaa acaggccgt acaaattgag aaacactacg gtcgcccgat ggatattgag    960
tgggcgaaag atggccacac cggtaaactg ttcattgtgc aggcgcgtcc ggaaaccgtg   1020
cgctcacgcg gtcaggtcat ggagcgttat acgctgcatt cacagggtaa gattatcgcc   1080
gaaggccgtg ctatcggtca tcgcatcggt gcgggtccgg tgaaagtcat ccatgacatc   1140
agcgaaatga accgcatcga acctggcgac gtgctggtta ctgacatgac cgacccggac   1200
tgggaaccga tcatgaagaa agcatctgcc atcgtcacca accgtggcgg tcgtacctgt   1260
cacgcggcga tcatcgctcg tgaactgggc attccggcgg tagtgggctg tggagatgca   1320
acagaacgga tgaaagacgg tgagaacgtc actgtttctt gtgccgaagg tgataccggt   1380
```

```
tacgtctatg cggagttgct ggaatttagc gtgaaaagct ccagcgtaga aacgatgccg    1440
gatctgccgt tgaaagtgat gatgaacgtc ggtaacccgg accgtgcttt cgacttcgcc    1500
tgcctaccga acgaaggcgt gggccttgcg cgtctggaat ttatcatcaa ccgtatgatt    1560
ggcgtccacc cacgcgcact gcttgagttt gacgatcagg aaccgcagtt gcaaaacgaa    1620
atccgcgaga tgatgaaagg ttttgattct ccgcgtgaat tttacgttgg tcgtctgact    1680
gaagggatcg cgacgctggg tgccgcgttt tatccgaagc gcgtcattgt ccgtctctct    1740
gattttaaat cgaacgaata tgccaacctg gtcggtggtg agcgttacga gccagatgaa    1800
gagaacccga tgctcggctt ccgtggcgcg ggccgctatg tttccgacag cttccgcgac    1860
tgtttcgcgc tggagtgtga agcagtgaaa cgtgtgcgca acgacatggg actgaccaac    1920
gttgagatca tgatcccgtt cgtgcgtacc gtagatcagg cgaaagcggt ggttgaagaa    1980
ctggcgcgtc agggggctga acgtggcgag aacgggctga aaatcatcat gatgtgtgaa    2040
atcccgtcca acgccttgct ggccgagcag ttcctcgaat atttcgacgg cttctcaatt    2100
ggctcaaacg atatgacgca gctggcgctc ggtctggacc gtgactccgg cgtggtgtct    2160
gaattgttcg atgagcgcaa cgatgcgtg aaagcactgc tgtcgatggc tatccgtgcc    2220
gcgaagaaac agggcaaata tgtcgggatt tgcggtcagg gtccgtccga ccacgaagac    2280
tttgccgcat ggttgatgga agaggggatc gatagcctgt ctctgaaccc ggacaccgtg    2340 gtgcaaaacct ggttaagcct ggctgaactg aagaaataa                          2379

<210> SEQ ID NO 20
<211> LENGTH: 2100
<212> TYPE: DNA
<213> ORGANISM: Bacillus subtilis 168

<400> SEQUENCE: 20
atgtttaaag cattattcgg cgttcttcaa aaaattgggc gtgcgcttat gcttccagtt      60
gcgatccttc cggctgcggg tattttgctt gcgatcggga atgcgatgca aaataaggac     120
atgattcagg tcctgcattt cttgagcaat gacaatgttc agcttgtagc aggtgtgatg     180
gaaagtgctg ggcagattgt tttcgataac cttccgcttc ttttcgcagt aggtgtagcc     240
atcgggcttg ccaatggtga tggagttgca gggattgcag caattatcgg ttatcttgta     300
atgaatgtat ccatgagtgc ggttcttctt gcaaacggaa ccattccttc ggattcagtt     360
gaaagagcca agttctttac ggaaaaccat cctgcatatg taaacatgct tggtataccct    420 accttggcga caggggtgtt cggcggtatt atcgtcggtg tgttagctgc attattgttt     480
aacagatttt acacaattga actgccgcaa taccttggtt tctttgcggg taaacgtttc     540
gttccaattg ttacgtcaat ttctgcactg attctgggtc ttattatgtt agtgatctgg     600
cctccaatcc agcatggatt gaatgccttt tcaacaggat tagtggaagc gaatccaacc     660
cttgctgcat ttatcttcgg ggtgattgaa cgttcgctta tcccattcgg attgcaccat     720
attttctatt caccgttctg gtatgaattc ttcagctata agagtgcagc aggagaaatc     780
atccgcgggg atcagcgtat ctttatggcg cagattaaag acggcgtaca gttaacggca     840
ggtacgttca tgacaggtaa atatccattt atgatgttcg gtctgcctgc tgcggcgctt     900
gccatttatc atgaagcaaa accgcaaaac aaaaaactcg ttgcaggtat tatgggttca     960
gcggccttga catctttctt aacggggatc acagagccat ggaattttc tttcttattc    1020 gttgctccag tcctgtttgc gattcactgt ttgtttgcgg actttcatt catggtcatg    1080
```

```
cagctgttga atgttaagat tggtatgaca ttctccggcg gtttaattga ctacttccta    1140
ttcggtattt taccaaaccg gacggcatgg tggcttgtca tccctgtcgg cttagggtta    1200
gcggtcattt actactttgg attccgattt gccatccgca aatttaatct gaaaacacct    1260
ggacgcgagg atgctgcgga agaaacagca gcacctggga aaacaggtga agcaggagat    1320
cttccttatg agattctgca ggcaatgggt gaccaggaaa acatcaaaca ccttgatgct    1380
tgtatcactc gtctgcgtgt gactgtaaac gatcagaaaa aggttgataa agaccgtctg    1440
aaacagcttg gcgcttccgg agtgctggaa gtcggcaaca acattcaggc tattttcgga    1500
ccgcgttctg acgggttaaa aacacaaatg caagacatta ttgcgggacg caagcctaga    1560
cctgagccga aacatctgc tcaagaggaa gtaggccagc aggttgagga agtgattgca    1620
gaaccgctgc aaaatgaaat cggcgaggaa gttttcgttt ctccgattac cggggaaatt    1680
cacccaatta cggatgttcc tgaccaagtc ttctcaggga aaatgatggg tgacggtttt    1740
gcgattctcc cttctgaagg aattgtcgta tcaccggttc gcggaaaaat tctcaatgtg    1800
ttcccgacaa aacatgcgat cggcctgcaa tccgacggcg aagagaaat tttaatccac    1860
tttggtattg ataccgtcag cctgaagggc gaaggattta cgtctttcgt atcagaagga    1920
gaccgcgttg agcctggaca aaaacttctt gaagttgatc tggatgcagt caaaccgaat    1980
gtaccatctc tcatgacacc gattgtattt acaaaccttg ctgaaggaga aacagtcagc    2040
attaaagcaa gcggttcagt caacagagaa caagaagata ttgtgaagat tgaaaaataa    2100

<210> SEQ ID NO 21
<211> LENGTH: 1803
<212> TYPE: DNA
<213> ORGANISM: Bacillus subtilis 168

<400> SEQUENCE: 21
ttgcaagaca tctacggaac tttagccaat ctgaacacga aattaaaaca aaagctgtct      60
catccttatt tagcgaagca tatttctgcg ccgaaaattg atgaggataa gcttcttctt     120
tttcatgctt tatttgaaga agccgacata aaaaacaacg acagagaaaa ttatattgta     180
acagcgatgc ttgtacaaag cgcccttgat acccatgatg aagtgacgac agctagagtc     240
ataaaacgag acgaaaacaa aaaccgccaa ttgactgttc tcgcgggcga ttatttcagc     300
gggctgtact actctttact atctgaaatg aaggatatct acatgattcg gacgcttgct     360
acagccatta agaaatcaa cgaacataaa attcgtctgt atgaccgttc tttcaaggac     420
gaaaacgatt ttttcgaaag tgtcggcatc gttgaatcag ctttattcca tcgtgtggcg     480
gaacacttca acctcccgcg ctggaaaaag ctgtcgagtg atttttttgt atttaagcgg     540
cttatgaacg gaaatgatgc atttctggat gtgatcggca gttttataca gctgggaaaa     600
acaaaagaag agatattaga agattgtttt aaaaaagcga aaaacagcat tgagtcactt     660
ctgcctctaa attcacctat tcagaacatt ttaataaacc gtctgaagac aatcagccaa     720
gatcaaacct atcatcagaa agtggaagaa gggtaaatgt taaatatcat tcgtttactg     780
gcggagtcgc tgccacgcat atcggatgga aatgaaaaca cagatgtttg ggtgaatgat     840
atgaaattta aaatggccta ctcttttta aatgacgata ttgatgtaat cgaaagagaa     900
cttgaacaaa ccgtacgttc cgattacccg cttttaagcg aggcaggtct tcacctgctg     960
caggccggag ggaaacgtat tcggcctgtt ttcgtgctgc tttctggcat gtttggcgat    1020
tatgatatta ataagattaa atatgtcgcc gtcactctgg aaatgattca catggcatct    1080
ttggttcatg atgatgtcat tgatgatgca gagcttcgcc gaggaaaacc gacaatcaaa    1140
```

```
gcaaagtggg acaatcgtat tgcgatgtac acaggcgatt atatgcttgc gggatctctt    1200
gaaatgatga cgagaattaa cgaaccgaaa gcccatagga ttttgtcaca gacgatcgtt    1260
gaagtttgtc tagggaaat tgagcagatc aaagacaaat acaacatgga acaaaatctc    1320
agaacgtatc tccgccgtat caaaagaaaa acagctctct tgatcgcggt cagctgccag    1380
cttggtgcca ttgcgtctgg agctgatgag aagattcata aggcattgta ctggtttggg    1440
tattacgtcg gcatgtctta tcagattatt gatgatattc ttgattttac ttcaactgag    1500
gaagagctgg gtaaacccgt aggaggagat ttgcttcaag gaaacgtcac attgccagtg    1560
ctgtatgccc tgaaaaatcc tgcattaaaa aaccagctta aattgattaa cagtgagaca    1620
acgcaggaac agcttgaacc aatcattgaa gaaatcaaaa aaacagatgc aattgaagca    1680
tctatggcag taagcgaaat gtatctgcag aaagcttttc agaaattaaa cacgcttcct    1740
cgagggcgcg cacgctcgtc tcttgcagcc atcgcaaaat atatcggtaa aagaaaattt    1800
taa                                                                 1803

<210> SEQ ID NO 22
<211> LENGTH: 1050
<212> TYPE: DNA
<213> ORGANISM: Bacillus subtilis 168

<400> SEQUENCE: 22
atgactcgag cagaacgaaa aagacaacac atcaatcatg ccttgtccat cggccagaag     60
cgggaaacag gtcttgatga tattacgttt gttcacgtca gtctgcccga tcttgcatta    120
gaacaagtag atatttccac aaaaatcggc gaactttcaa gcagttcgcc gatttttatc    180
aatgcaatga ctggcggcgg cggaaaactt acatatgaga ttaataaatc gcttgcgcga    240
gcggcttctc aggctggaat tccccttgct gtgggatcgc aaatgtcagc attaaaagat    300
ccatcagagc gtctttccta tgaaattgtt cgaaaggaaa acccaaacgg gctgattttt    360
gccaacctgg gaagcgaggc aacggctgct caggcaaagg aagccgttga gatgattgga    420
gcaaacgcac tgcagatcca cctcaatgtg attcaggaaa ttgtgatgcc tgaaggggac    480
agaagcttta gcggcgcatt gaaacgcatt gaacaaattt gcagccgggt cagtgtaccg    540
gtcattgtga aagaagtcgg cttcggtatg agcaaagcat cagcaggaaa gctgtatgaa    600
gctggtgctg cagctgttga cattggcggt tacggggaa caaatttctc gaaaatcgaa    660
aatctccgaa gacagcggca aatctccttt tttaattcgt ggggcatttc gacagctgca    720
agtttggcgg aaatccgctc tgagtttcct gcaagcacca tgatcgcctc tggcggtctg    780
caagatgcgc ttgacgtggc aaaggcaatt gcgctggggg cctcttgcac cggaatggca    840 gggcatttt taaaagcgct gactgacagc ggtgaggaag gactgcttga ggagattcag    900
ctgatccttg aggaattaaa gttgattatg accgtgctgg gtgccagaac aattgccgat    960
ttacaaaagg cgccccttgt gatcaaaggt gaaaccatc attggctcac agagagaggg    1020
gtcaatacat caagctatag tgtgcgataa                                    1050
```